(12) United States Patent
Landry et al.

(10) Patent No.: US 11,850,171 B2
(45) Date of Patent: Dec. 26, 2023

(54) WATERPROOF PROSTHETIC KNEE AND REMOVABLE COVERING THEREFOR

(71) Applicant: Össur Iceland ehf, Reykjavik (IS)

(72) Inventors: David Landry, Reykjavik (IS); Gudni Ingimarsson, Reykjavik (IS); Gunnar Omar Lillie Magnusson, Reykjavik (IS); Lucas Ikelaar, Reykjavik (IS); Sylvain Gagné, Reykjavik (IS); Kristin Asa Thorisdottir, Reykjavik (IS)

(73) Assignee: Össur Iceland ehf, Reykjavik (IS)

( * ) Notice: Subject to any disclaimer, the term of this patent is extended or adjusted under 35 U.S.C. 154(b) by 24 days.

(21) Appl. No.: 17/685,193

(22) Filed: Mar. 2, 2022

(65) Prior Publication Data

US 2022/0280315 A1 Sep. 8, 2022

Related U.S. Application Data

(60) Provisional application No. 63/273,569, filed on Oct. 29, 2021, provisional application No. 63/200,381, filed on Mar. 3, 2021.

(51) Int. Cl.
*A61F 2/64* (2006.01)
*A61F 2/78* (2006.01)
(Continued)

(52) U.S. Cl.
CPC ............... *A61F 2/64* (2013.01); *A61F 2/70* (2013.01); *A61F 2/78* (2013.01);
(Continued)

(58) Field of Classification Search
CPC ...... A61F 2/64; A61F 2/70; A61F 2/78; A61F 2002/5001; A61F 2002/5004; A61F 2002/6818; A61F 2002/701
See application file for complete search history.

(56) References Cited

U.S. PATENT DOCUMENTS 6,610,101 B2 8/2003 Herr et al.
6,764,520 B2 7/2004 Deffenbaugh et al.
(Continued)

FOREIGN PATENT DOCUMENTS

DE 102016119001 A1 4/2018
EP 0056602 A1 7/1982
WO WO-2014033876 A1 * 3/2014 ............... A61F 2/64

OTHER PUBLICATIONS

International Search Report and Written Opinion Received in PCT Application No. PCT/IB2022/051818 dated May 17, 2022 in 11 pages.

*Primary Examiner* — Bruce E Snow
(74) *Attorney, Agent, or Firm* — Knobbe, Martens, Olson & Bear LLP

(57) ABSTRACT

A prosthetic knee can include a variable-torque magnetorheological (MR) actuator assembly or braking system, a frame and an electronics assembly or system that also serves as a mount for the knee actuator and facilitates in monitoring and controlling the operation of the knee actuator. The prosthetic knee system advantageously provides resistive forces to substantially simulate the position and motion of a natural knee joint during ambulation and/or other locomotory activities performed by the amputee. The prosthetic knee can be enclosed in a waterproof compartment. An outer cover can be configured to fit around the waterproof cover of the prosthetic knee.

20 Claims, 25 Drawing Sheets

(51) Int. Cl.
*A61F 2/70* (2006.01)
*A61F 2/50* (2006.01)
*A61F 2/68* (2006.01)

(52) U.S. Cl.
CPC ........ *A61F 2002/5001* (2013.01); *A61F 2002/5004* (2013.01); *A61F 2002/6818* (2013.01); *A61F 2002/701* (2013.01)

(56) References Cited

U.S. PATENT DOCUMENTS

| | | |
|---|---|---|
| 7,101,487 B2 | 9/2006 | Hsu et al. |
| 7,198,071 B2 | 4/2007 | Bisbee, III et al. |
| 7,455,696 B2 | 11/2008 | Bisbee, III et al. |
| 7,691,154 B2 | 4/2010 | Asgeirsson et al. |
| 9,956,093 B1 * | 5/2018 | Harris ................ A61F 2/76 |
| 2006/0136072 A1 | 6/2006 | Bisbee et al. |
| 2015/0250622 A1 | 9/2015 | Nakaya et al. |

* cited by examiner

WATERPROOF PROSTHETIC KNEE AND REMOVABLE COVERING THEREFOR

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND

Field

The present invention relates to prosthetic devices in general and, in particular, to magnetorheologically actuated controllable braking systems utilized in prosthetic knees.

Description of the Related Art

Three types of variable-torque brakes have been employed in prosthetic knees in the past: (i) dry friction brakes where one material surface rubs against another surface with variable force; (ii) viscous torque brakes using hydraulic fluid squeezed through a variable sized orifice or flow restriction plate; and (iii) magnetorheological (MR) brakes or dampers where MR fluid (containing small iron particles suspended in the fluid) is squeezed through a fixed orifice or flow restriction plate, with viscosity of the fluid being varied in response to an applied magnetic field. Each of these technologies, as conventionally practiced in the field of prosthetics, can pose certain disadvantages.

Though dry friction brakes can generally provide a substantial torque range for their size, undesirably, they are often difficult to control. After extended use, the frictional pads tend to wear, thereby changing the frictional characteristics of the brake and the torque response for a given commanded torque. Disadvantageously, this can cause unreliable damping performance, and hence adversely affect the gait of the amputee and also cause discomfort to the amputee. Consequently, dry friction brakes may need frequent servicing and/or replacement which undesirably adds to the cost.

Under high loading conditions, viscous torque brakes are susceptible to leakage of hydraulic fluid and possibly other damage due to excessive pressure build-up. Disadvantageously, this can result in an irreversible state, since once the brake unit is overloaded it cannot return to normal. Therefore, such a viscous torque brake for a prosthetic joint is prone to catastrophic failure, and hence can be unreliable and detrimental to the safety of an amputee.

In certain MR brakes and dampers, the interaction of the MR fluid with the device undesirably causes increased pressure, seal deterioration, or a combination of the two. Another possible cause of these adverse effects is decomposition of the MR fluid. Once the seals fail or the MR fluid decomposes, the prosthetic knee is no longer suitable for use.

SUMMARY

In accordance with one aspect of the disclosure, a prosthetic knee with a waterproof cover is provided. The waterproof cover can be waterproof to a depth of three meters for up to one hour or can be waterproof to a depth of four meters for up to one hour and thirty minutes.

In accordance with another aspect of the disclosure, a prosthetic knee with a waterproof cover is provided. The waterproof cover can have an upper portion that can translate and/or tilt relative to lower portion.

In accordance with another aspect of the disclosure, a prosthetic knee with a removable cosmetic cover is provided. The cosmetic cover can wrap around at least a portion of the prosthetic knee and has a closing interface that allows opposite sides of the cosmetic cover to releasably couple to each other.

In accordance with another aspect of the disclosure, a prosthetic knee with an elongate frame configured to house electronics, an actuator movably coupled to a proximal portion of the elongate frame, the actuator rotatable in an anterior-posterior direction about a medial-lateral axis, the actuator comprising an outer spline, a proximal connector coupled to the outer spline and configured to rotate with the outer spline about the medial-lateral axis, and a distal connector coupled to a distal end of the elongate frame is provided. The prosthetic knee can further include a waterproof cover assembly coupled to the actuator and the frame. The waterproof cover assembly can have a proximal cover portion couplable to a medial side and a lateral side of the actuator via one or more waterproof seals, and a distal cover portion. The distal cover portion can be configured to enclose a distal portion of the frame and can be configured to couple to the distal connector via one or more waterproof seals. A proximal end of the distal cover portion can be movably coupled to a distal end of the proximal cover portion. One or more waterproof seals can be disposed between the distal end of the proximal cover portion and proximal end of the distal cover portion.

In accordance with another aspect of the disclosure, a prosthetic knee with an elongate frame configured to house electronics, an actuator movably coupled to a proximal portion of the elongate frame, the actuator rotatable in an anterior-posterior direction about a medial-lateral axis, the actuator comprising an outer spline, a proximal connector coupled to the outer spline and configured to rotate with the outer spline about the medial-lateral axis, a distal connector coupled to a distal end of the elongate frame, and a removable cover is provided. The prosthetic knee can further include a waterproof cover assembly coupled to the actuator and the frame. The waterproof cover assembly can have a proximal cover portion couplable to a medial side and a lateral side of the actuator via one or more waterproof seals, and a distal cover portion. The distal cover portion can be configured to enclose a distal portion of the frame and can be configured to couple to the distal connector via one or more waterproof seals. A proximal end of the distal cover portion can be movably coupled to a distal end of the proximal cover portion. One or more waterproof seals can be disposed between the distal end of the proximal cover portion and proximal end of the distal cover portion.

In accordance with another aspect of the disclosure, a prosthetic knee is provided. The prosthetic knee can include an elongate frame that can house electronics, an upper enclosure, and an outer cover. The upper enclosure can include an actuator coupled to a proximal portion of the elongate frame, where the actuator is rotatable in an anterior-posterior direction about a medial-lateral axis. The upper enclosure can further include a first side mount including a first groove extending at least partially about the circumference of the first side mount. The outer cover can be coupled to the upper enclosure and the elongate frame and include a proximal portion including a first lip. The first lip can at least partially extend into the first groove of the first side mount of the upper enclosure to removably couple the proximal portion of the outer cover to the upper enclosure.

A contour of the first lip can correspond to a contour of the first groove. The first groove can include a first adaptor, and a contour of the first adaptor can correspond to a contour of the first lip. The first adaptor can include a first protrusion positioned between two adjacent lower portions. The first lip can include a first recess positioned between two adjacent flaps. A contour of the first protrusion and the adjacent lower portions can correspond to a contour of the first recess and the adjacent flaps. The first adaptor can include a first leg that can at least partially extend into a slot formed on the first side mount to couple the first adaptor to the first side mount.

The upper enclosure can include a second side mount comprising a second groove. The second groove can extend at least partially about the circumference of the second side mount. The proximal portion of the outer cover can include a second lip that can at least partially extend into the second groove of the second side mount to removably couple the proximal portion of the outer cover to the upper enclosure. The second groove can include a second adaptor, and a contour of the second adaptor can correspond to a contour of the second lip.

The first side mount can be positioned on a lateral side of the actuator. The second side mount can be positioned on a medial side of the actuator.

The outer cover can include a toggle cover portion, a button, and a flexible membrane. The button can be connected to the outer cover via the flexible membrane, and the toggle cover portion can be positioned on top of an outer surface of the button. The flexible membrane can include a flex portion and can bias the button to an unactuated position. In response to toggle cover portion being pushed inwards, the flexible membrane can flex inward to allow the button to engage a position lock control for the actuator of the prosthetic knee.

The prosthetic knee can further include a proximal connector and a distal connector. The proximal connector can be coupled to the actuator and configured to rotate with the actuator about the medial-lateral axis. The distal connector can be coupled to a distal portion of the elongate frame.

In accordance with another aspect of the disclosure, a prosthetic knee is provided. The prosthetic knee can include an elongate frame that can house electronics, an upper enclosure, and an outer cover. The upper enclosure can include an actuator coupled to a proximal portion of the elongate frame. The upper enclosure can include a first groove and a second groove, where the first groove is positioned on a lateral side of the actuator and the second groove is positioned on a medial side of the actuator. The outer cover can be coupled to the upper enclosure and the elongate frame and include a first lip and a second lip. The first lip can at least partially extend into the first groove and the second lip can at least partially extend into the second groove to removably couple the outer cover to the upper enclosure.

The actuator can be rotatable in an anterior-posterior direction about a medial-lateral axis. The upper enclosure can include a first side mount and a second side mount. The first groove can extend at least partially about the circumference of the first side mount, and the second groove can extend at least partially about the circumference of the second side mount.

In accordance with another aspect of the disclosure, an outer cover for a prosthetic knee is provided. The outer cover can include a proximal portion that can enclose an upper enclosure of a prosthetic knee and be coupled to a first side mount and a second side mount of the upper actuator. The proximal portion can include a first lip and a second lip, where the first lip can at least partially extend into a first groove of the first side mount and the second lip can at least partially extend into a second groove of the second side mount. A contour of the first lip can correspond to that of the first groove and a contour of the second lip can correspond to that of the second groove.

The first groove can include a first adaptor and the second groove comprises a second adaptor. The contour of the first lip can correspond to that of the first adaptor, and the contour of the second lip can correspond to that of the second adaptor. The first groove can extend at least partially about the circumference of the first side mount, and the second groove can extend at least partially about the circumference of the second side mount. The first side mount can be positioned on a lateral side of the actuator, and the second side mount can be positioned on a medial side of the actuator. The first lip can include a first recess, the first groove can include a first adaptor comprising a first protrusion, and the first recess can receive the first protrusion to allow the first groove to receive the first lip.

The systems and methods for limb support devices and sole systems—disclosed herein have several features, no single one of which is solely responsible for their desirable attributes. Without limiting the scope as expressed by the claims that follow, certain features of the limb support devices and the sole systems will now be discussed briefly. One skilled in the art will understand how the features of the disclosed technology provide several advantages over traditional systems and methods.

In accordance with another aspect of the disclosure, a prosthetic knee is provided. The prosthetic knee comprises an elongate frame configured to house electronics, and an actuator movably coupled to a proximal portion of the elongate frame, the actuator being rotatable in an anterior-posterior direction about a medial-lateral axis, the actuator comprising an outer spline. The prosthetic knee also comprises a proximal connector coupled to the outer spline and configured to rotate with the outer spline about the medial-lateral axis, and a distal connector coupled to a distal end of the elongate frame. The prosthetic knee also comprises a waterproof cover assembly movably coupled to the actuator and the elongate frame. The waterproof cover assembly comprises an upper housing including an upper enclosure couplable to a medial side and a lateral side of the actuator via one or more waterproof seals, and a lower housing configured to enclose a distal portion of the elongate frame and configured to couple to the distal connector via one or more waterproof seals.

In accordance with another aspect of the disclosure, a prosthetic knee is provided. The prosthetic knee comprises an elongate frame configured to house electronics. The prosthetic knee also comprises an upper enclosure comprising an actuator coupled to a proximal portion of the elongate frame, the actuator being rotatable in an anterior-posterior direction about a medial-lateral axis. The upper enclosure includes a medial side mount and lateral side mount, a first groove extending at least partially about a circumference of the medial side mount, and a second groove extending at least partially about a circumference of the lateral side mount. The prosthetic knee also comprises an outer cover coupled to the upper enclosure and over the elongate frame. The outer cover comprises a proximal portion comprising a first lip configured to at least partially extend into the first groove and a second lip configured to at least partially extend into the second groove to removably couple the proximal portion of the outer cover to the upper enclosure.

DETAILED DESCRIPTION

Understanding normal human walking/running provides the basis for the design and development of effective lower limb prostheses with controlled motion. Normal human locomotion or gait can be described as a series of rhythmical alternating movements of the limbs and trunk which result in the forward progression of the body's center of gravity.

Figure 1:
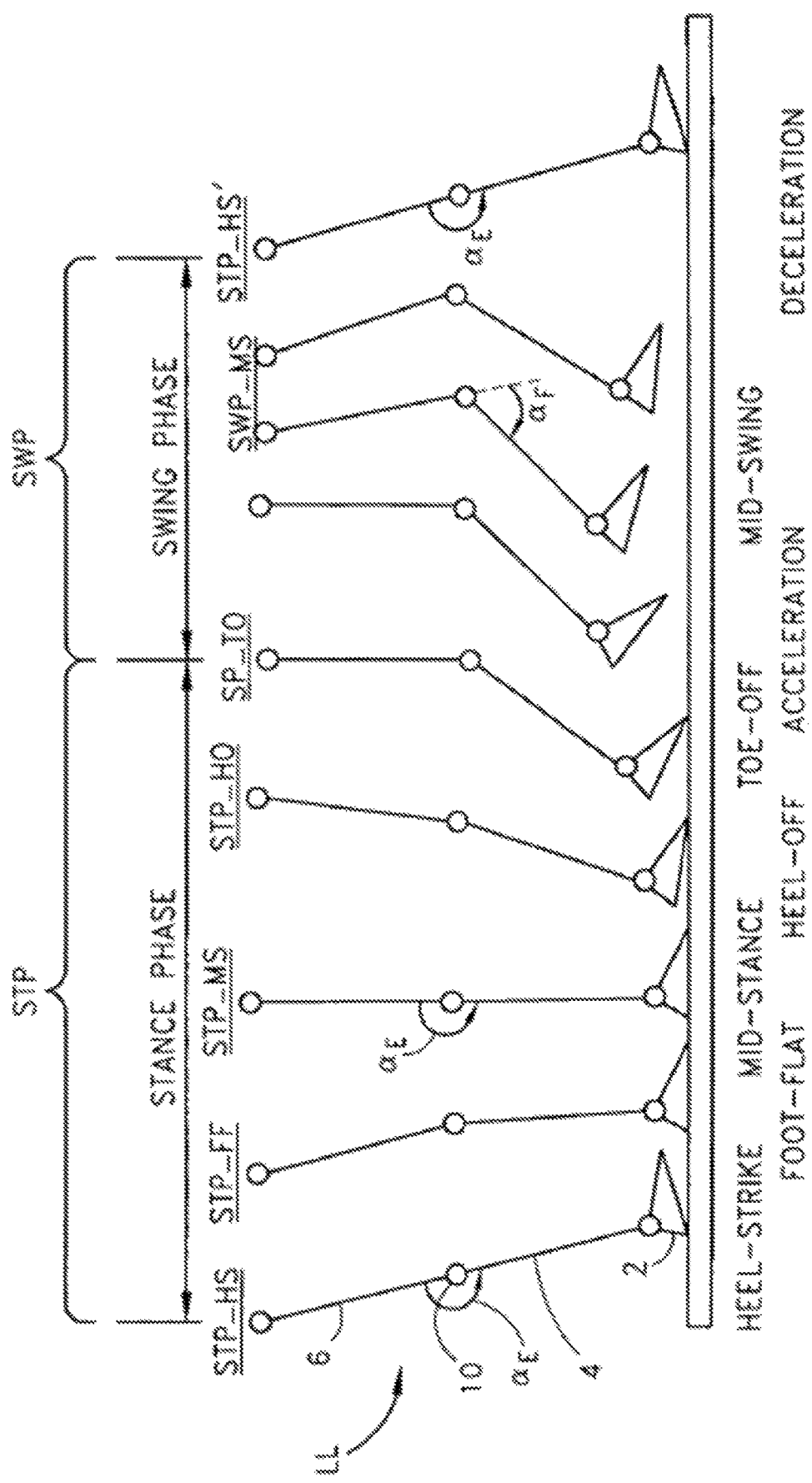
FIG. 1 is a schematic view of one normal human locomotion cycle illustrating the various limb positions during stance and swing phases.

One typical gait cycle, as schematically depicted in FIG. 1, comprises of the activity that occurs between heel strike of one lower limb LL and the subsequent heel strike of the same limb LL. The limb or leg LL generally comprises a foot 2 and a shin portion 4 coupled or articulated to a thigh portion 6 via a knee or knee joint 10. During a single gait cycle each lower limb or extremity passes through one stance or extended phase STP and one swing phase SWP.

The stance phase STP begins at heel-strike STP_HS when the heel touches the floor or supporting ground surface and the stance knee begins to flex slightly. This flexion allows for shock absorption upon impact and also maintains the body's center of gravity at a more constant vertical level during stance.

Shortly after heel-strike STP_HS, the sole makes contact with the ground at the beginning of the foot-flat phase STP_FF. After maximum flexion is reached in the stance knee, the joint begins to extend again, until maximum extension is reached at mid-stance STP_MS as the body weight is swung directly over the supporting extremity and continues to rotate over the foot.

As the body mass above the ankle continues to rotate forward, the heel lifts off the ground at heel-off STP_HO. Shortly after this, the body is propelled forward by the forceful action of the calf-muscles (push-off). The push-off phase terminates when the entire foot rises from the ground at toe-off SP_TO.

During late stance, the knee of the supporting leg flexes in preparation for the foot leaving the ground for swing. This is typically referred to in the literature as "knee break". At this time, the adjacent foot strikes the ground and the body is in "double support mode", that is, both the legs are supporting the body weight.

At toe-off SP_TO, as the hip is flexed and the knee reaches a certain angle at knee break, the foot leaves the ground and the knee continues to flex into the swing phase. During early swing the foot accelerates. After reaching maximum flexion at mid-swing SWP_MS, the knee begins to extend and the foot decelerates. After the knee has reached full extension, the foot once again is placed on the ground at heel-strike STP_HS' and the next walking cycle begins.

Typically, the anatomical position is the upright position, therefore flexion is a movement of a body part away from the extended or stance or anatomical position. Thus, bending of the knee is knee flexion. Extension is a movement of a limb towards the anatomical position, thus knee extension is a movement in the "straightening" direction.

During a typical normal walking progression on a generally level surface, the maximum flexion angle $\alpha F$ varies between about 50° and 80°. The maximum extension angle $\alpha E$ is typically about or close to 180°. Thus, in level walking the normal human knee rotates through a range of approximately 50°-80° going from a position of full extension in early and mid-stance to 50°-80° of flexion shortly after toe-off. In other situations, such as, in a sitting position, the maximum flexion angle $\alpha F$ can be greater than about 50°-80° and up to, for example, about 140°-150°.

Figure 2:
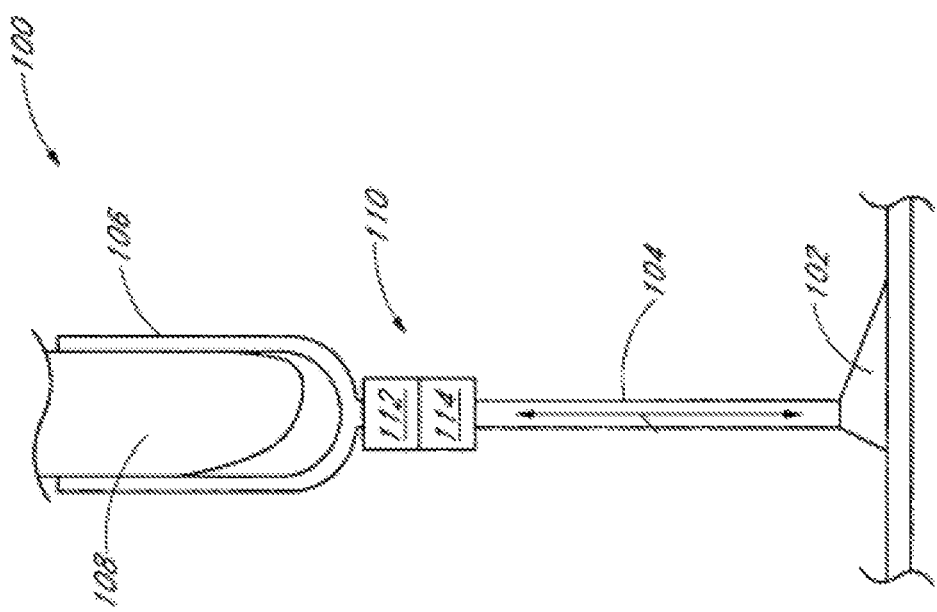
FIG. 2 is a schematic illustration of a lower limb prosthetic assembly, system or prosthesis.

FIG. 2 is a schematic illustration of a lower limb prosthetic assembly, system or prosthesis 100 including an electronically controlled active knee prosthetic assembly, system or prosthesis 110. As described in greater detail later herein, advantageously, the knee prosthesis 110 provides resistive forces to substantially simulate the position and motion of a natural knee joint during ambulation and/or other locomotory or stationary activities performed by an amputee. The prosthetic or artificial knee 110 is desirably safe, reliable and generally comfortable to use by the amputee.

The prosthetic lower limb 100 further includes an artificial or prosthetic foot 102 coupled or mechanically connected to a pylon, tube, shaft or shank portion 104 that connects to a distal or bottom portion of the prosthetic knee 110 and a residual limb or stump socket 106 that connects to a top or proximal end of the prosthetic knee 110. The stump socket 106 receives a residual limb or femur portion 108 of the amputee. A suitable pylon or the like can also be provided between the stump socket 106 and the prosthetic knee 110, as needed or desired. In some embodiments, the prosthetic knee 110 can be coupled to the user by osseointegration.

Embodiments of the invention can be practiced with a wide variety of prosthetic feet. These include Pro-Flex® Pivot, Pro-Flex® LP Align, Pro-Flex® LP Torsion, PRO-PRIO FOOT®, Pro-Flex® XC Torsion, Pro-Flex® LP, Pro-Flex® XC, Balance™ Foot S Torsion, Balance™ Foot S, Vari-Flex® Junior, LP Vari-Flex®, Vari-Flex®, Vari-Flex® Modular, Talux®, Re-Flex Shock™, Re-Flex Rotate™, Balance™ Foot J, Flex-Foot® Junior, Flex-Foot Balance® with D/P Flexion™, Flex-Foot Assure®, Flex-Foot Balance®, K2 Sensation®, K2 Sensation® with D/P Flexion™.

The prosthetic knee 110 includes a variable-torque magnetorheological (MR) actuator assembly or braking system 112 and a frame and electronics assembly or system 114 that also serves as a mount for the knee actuator 112 and facilitates in monitoring and controlling the operation of the knee actuator 112. The prosthetic knee system 110 advantageously provides resistive forces to substantially simulate the position and motion of a natural knee joint during ambulation and/or other locomotory activities performed by the amputee.

Advantageously, the prosthetic knee 110 permits the amputee to move and/or adapt comfortably and safely in a wide variety of circumstances. For example, during walking, running, sitting down, or when encountering subtle or drastic changes in the terrain, topography and environment or ambient conditions, such as, when the user lifts a suitcase or walks down a slope or encounters stairs, among others.

The prosthetic knee 110 provides stance control to limit buckling when weight is applied to the limb. In addition, the prosthetic knee 110 provides aerial swing control so that the knee reaches full extension just prior to or at heel-strike in a smooth and natural manner. Moreover, the prosthetic knee 110, by adjusting and/or fine tuning the range and/or magnitudes of the resistive torque level, can be adapted for use with a wide variety of patients having different body weights, heights and activity levels.

In some implementations, the prosthetic knee assembly 110 has particular efficacy when used in conjunction with a trans-femoral (above-knee, A/N) amputee. In modified embodiments, the prosthetic knee joint 110 may be efficaciously adapted for use with a knee-disarticulation (K/D) amputee wherein the amputation is through the knee joint, as needed or desired.

In some embodiments, the variable-torque magnetorheological (MR) actuator assembly or braking system 112 can contain a magnetorheological (MR) fluid. The MR fluid is a field responsive (FR) fluid or medium that undergoes a rheology or viscosity change which is dependent on the magnitude of the applied magnetic field. In turn, this variation in fluid viscosity determines the magnitude of the shearing force/stress, torque or torsional resistance generated, and hence the level of damping provided by the knee actuator 112 and/or the prosthetic knee 110. The resistive braking effect is a function of the MR fluid viscosity which in turn is a function of the magnetic field. Thus, by controlling the magnitude of this magnetic field, the rotary motion of the artificial limb is controlled, for example, to control the flexion and extension during swing and stance phases to provide a more natural and safe ambulation for the amputee.

The MR fluid generally comprises polarizable particles, a carrier fluid, and optionally an additive. In some embodiments, as described further below, the MR fluid is specifically designed for use in a shear mode device, such as the prosthetic knee 110. For such a device, mechanically hard particles are desired. The carrier fluid also desirably experiences a less dramatic viscosity change over temperature changes as compared to other fluids.

In some embodiments, the MR fluid has one or more of the following properties: a high magnetic flux capacity and low magnetic remanence and low viscosity while having a large magnetic field induced shearing stress. Advantageously, this allows the prosthetic knee 110 to provide a wide dynamic torque range.

Figure 3:
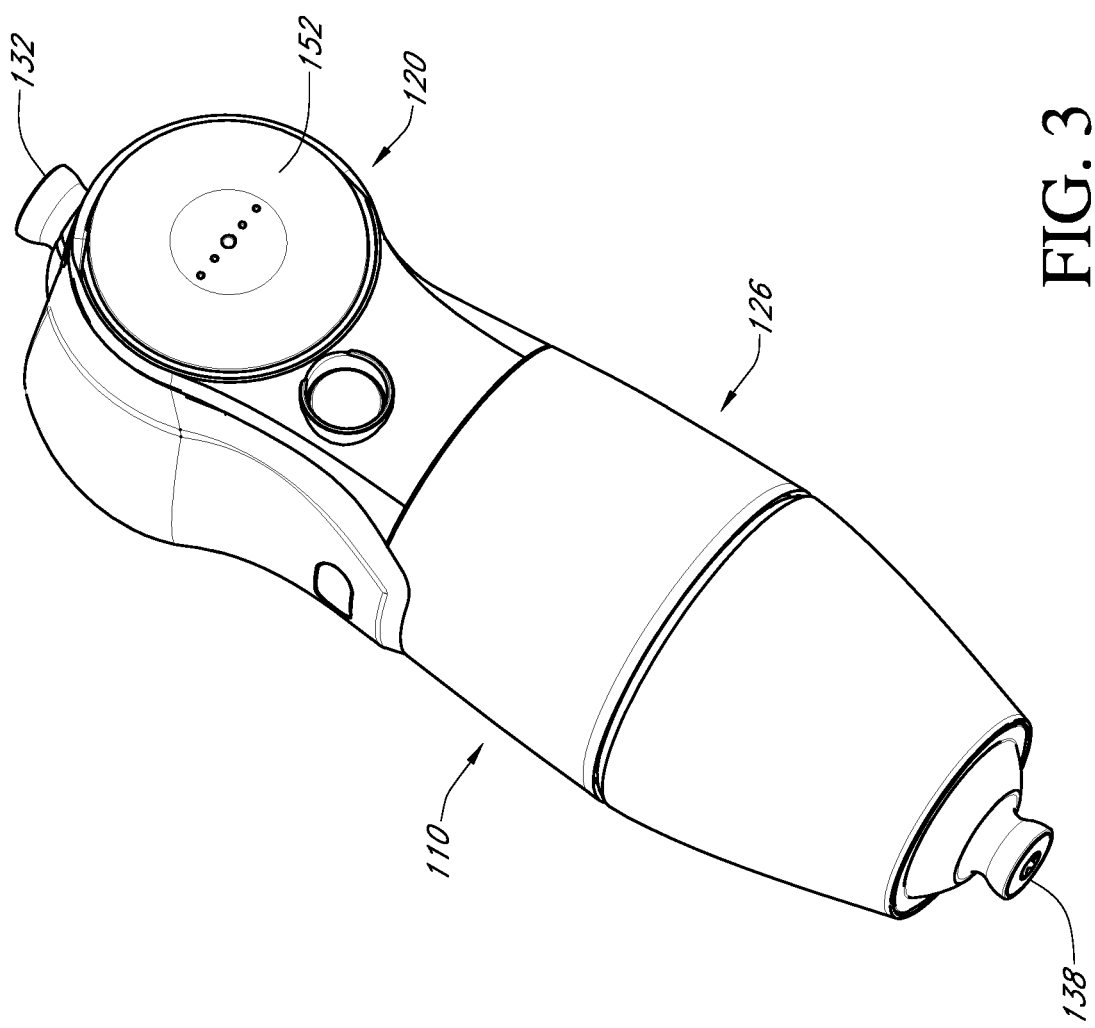
FIG. 3 is a perspective view of a prosthetic knee assembly.

FIG. 3. depicts an embodiment of the prosthetic knee 110. The internal components of the knee 110 are inside the upper enclosure 120 and the lower enclosure 126. For example, in some embodiments the knee actuator 112 may be at least partially (e.g., completely) inside the upper enclosure 120 and the electronic assembly 114 may be at least partially (e.g., completely) inside the lower enclosure. In other embodiments, both the electronic assembly 114 and knee actuator 110 may be inside the upper enclosure 120. In the depicted embodiment, the top pyramid connector 132 can protrude from the upper enclosure 120. The bottom pyramid connector 138 can protrude from the lower enclosure 126.

Figure 4:
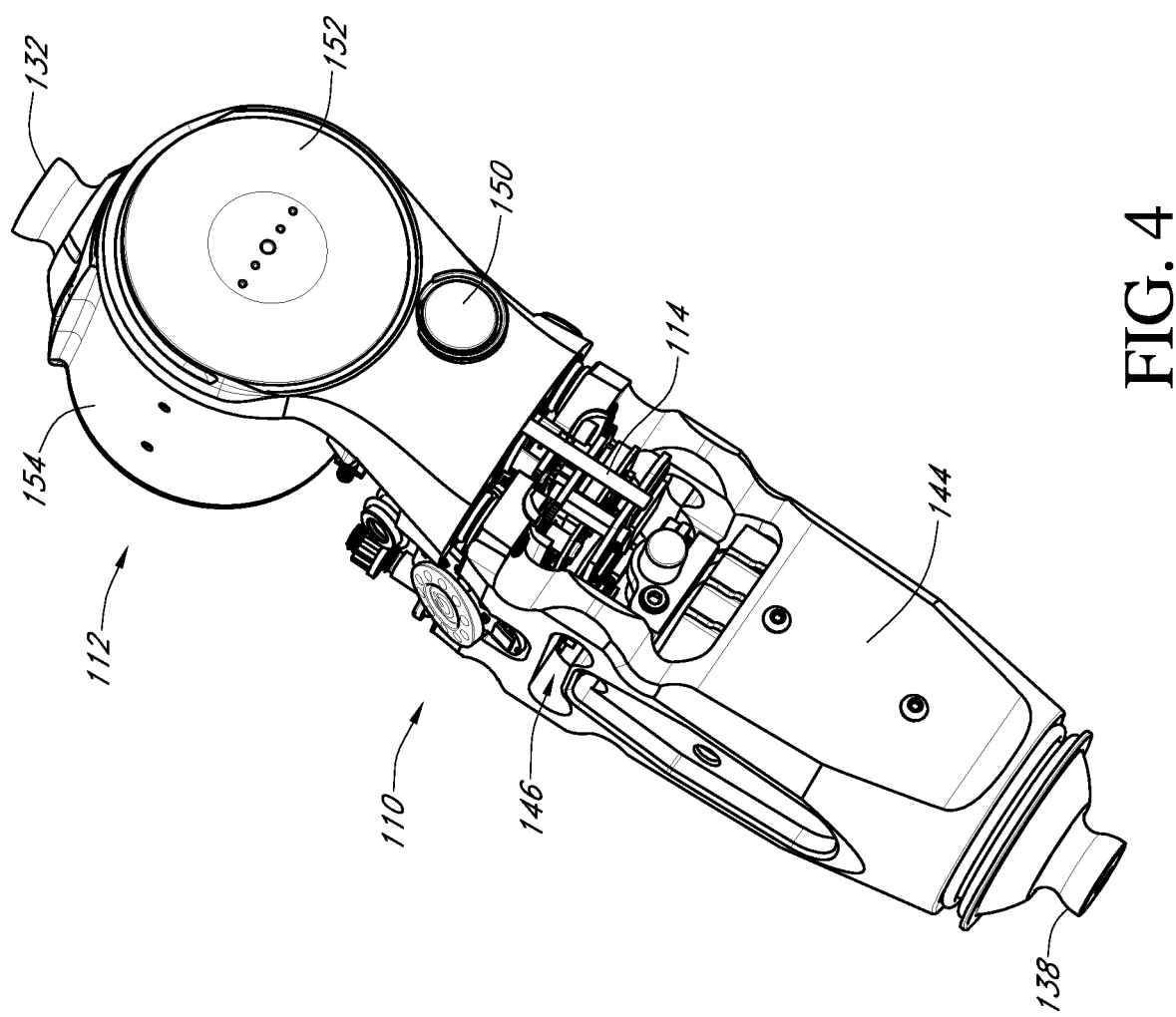
FIG. 4 is a perspective view of a prosthetic knee assembly of FIG. 3, with a distal cover portion removed.

FIG. 4. depicts the prosthetic knee 110 with portions of the outer covering not shown. The prosthetic knee assembly 110 includes the magnetorheological actuator assembly or system 112, the frame 144 (e.g., elongate frame) and electronics assembly or system 114. The frame 144 maintains a rigid shape to protect the electronic assembly 114 and to enable knee 110 usage. The knee actuator 112 rotates relative to the frame 144. The frame 144 can also contain a load cell 146. The electronics assembly 114 provides power and communicates with the actuator assembly 112 via electrical signals. The shown embodiment further depicts a position lock control 150 operable by a user. The position lock control 150 can be toggled to lock the knee actuator 110 in one or more rotational positions relative to the frame 144, as further described below. In some embodiments, the position lock control 150 is toggled by sliding the position lock control 150 from side-to-side (e.g., in a medial-lateral direction). In some embodiments, a user can determine the locked status of the position lock control 150 by visual inspection (e.g., of the position of the lock control 150).

The knee actuator 112 couples to a pair of side mounts 152 (only one shown), walls or forks that are mechanically coupled, communicated or connected to a core component and rotate with the core component about the knee joint axis of rotation. The side mounts 152 in combination with the outer spline 154 can form one main outer shell of the knee actuator 112. In some embodiments the outer spline 154 and the side mounts 152 form at least part of (e.g., all of) the upper enclosure 120. The side mounts 152 are connected to the frame 144 and electronics assembly 114, which in turn is connected to a lower (below the knee) part of the leg (not shown). Thus, rotation of the side mounts 152 corresponds to rotation of the lower part of the leg. The knee actuator 112 permits relative rotation between the side mounts 152 and the outer spline 154. The outer spline 154 is generally fixed relative to the upper leg (not shown) of the user. The side mounts 152 are generally fixed relative to the lower leg of the user (e.g., in one implementation the side mounts 152 do not rotate relative to the rest of the prosthetic knee 110, but include a bearing that allows rotation of the knee actuator 112 that extends between the side mounts 152).

A. Waterproof Prosthetic Knee

Figure 5:
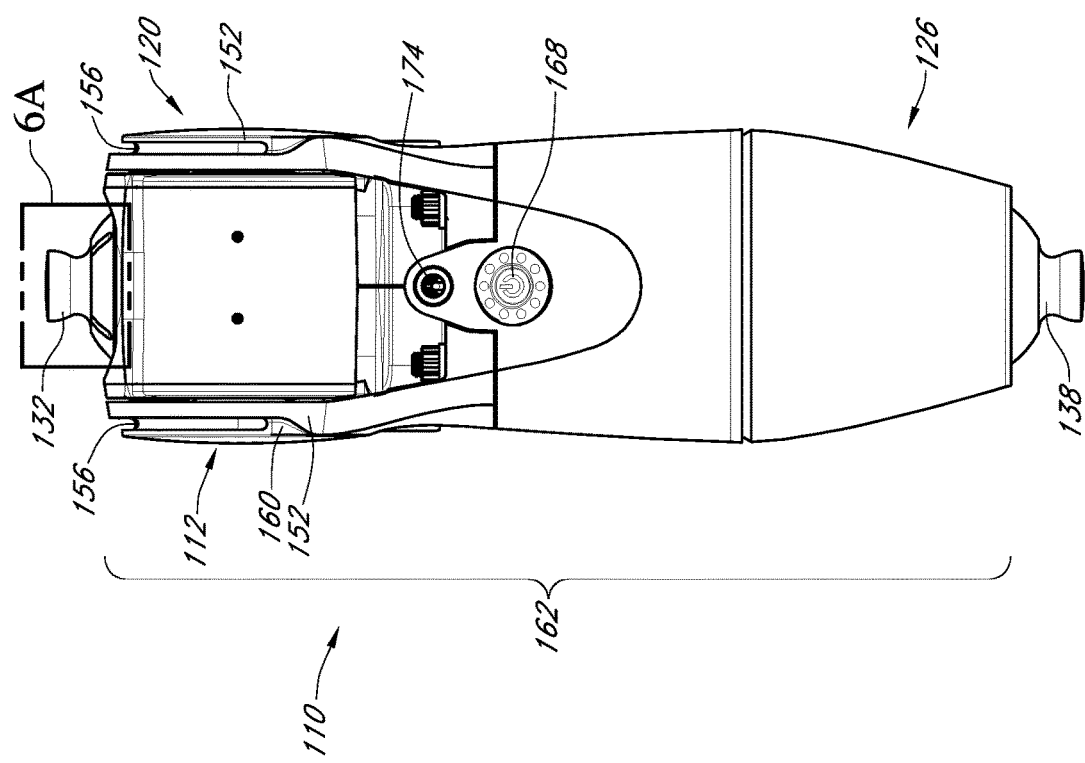
FIG. 5 is a front view of the prosthetic knee assembly of FIG. 3.

FIG. 5. depicts an embodiment of the prosthetic knee 110 that is waterproof. The top of the knee 110 can have grooves 156 disposed to either side of the top pyramid connector 132. The grooves 156 can be formed as part of the upper enclosure 120. Specifically, the grooves 156 can be formed as part of the side mounts 152 (see FIG. 6B). In some embodiments, the grooves 156 may extend towards the back and front of the prosthetic knee 110. The grooves 156 can extend in a circumferential direction, at least partially (e.g., completely) around the axis of rotation of the knee actuator 112. The grooves 156 can have a depth that varies or is constant. The groove 156 may be straight or curved. For example, the groove 156 may have a constant depth for a first circumferential distance, and a second depth for a second circumferential distance. In some embodiments, the groove 156 may be directed circumferentially for a first portion, and may be oriented axially (e.g., parallel to the axis of rotation of the knee actuator 112), or in a direction between the circumferential and axial direction for a second portion.

The upper enclosure 120 and lower enclosure 126 can cooperate to form a single waterproof compartment 162. In some embodiments, the waterproof compartment 162 may be waterproof at a depth of three meters for up to one hour. In some embodiments, the waterproofing compartment 162 may be waterproof at a depth of four meters for up to one hour and thirty minutes. Disposed on, accessible through, or formed as part of the waterproof compartment can be a control button 168 and a charger port 174. In some embodiments, the control button 168 may be functional to provide various commands to the prosthetic knee 110 (e.g., power on or power off commands). The charger port 174 can be functional to provide indications of the status of the prosthetic knee 110.

The waterproof compartment 162 can be made of various materials. The waterproof compartment 162 can be made of more than one material. For example, the side mount 152 can be made out of carbon filled thermoplastic (e.g., carbon filled thermoplastic polyurethane) or glass filled thermoplastic. The carbon filled thermoplastic or glass filled thermoplastic can be suitable for the side mount 152 because the side mount 152 is a structural part that can have substantial loading. Parts of the lower enclosure 126 can be made out of non-magnetic metal (e.g., aluminum). Parts of the lower enclosure 126 can be made out of polycarbonate blend (e.g., acrylonitrile butadiene styrene polycarbonate). In some embodiments, one or more parts of the upper enclosure 120 can be made out of non-magnetic metal (e.g., aluminum). Alternatively, one or more parts of the upper enclosure 120 can be made out of polycarbonate blend (e.g., acrylonitrile butadiene styrene polycarbonate). The waterproof compartment 162 can be composed of a higher strength material for the side mount 152, and a lower strength material for the lower enclosure 126.

Figure 6A:
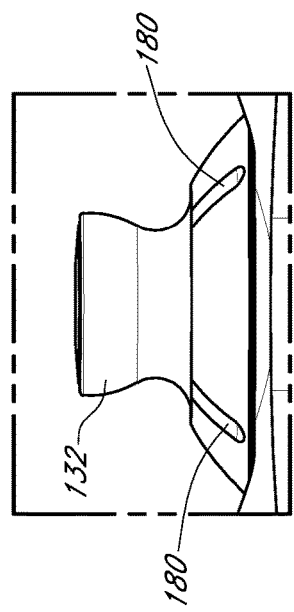
FIG. 6A is a front view of a pyramid connector of the prosthetic knee assembly of FIG. 3.
Figure 6C:
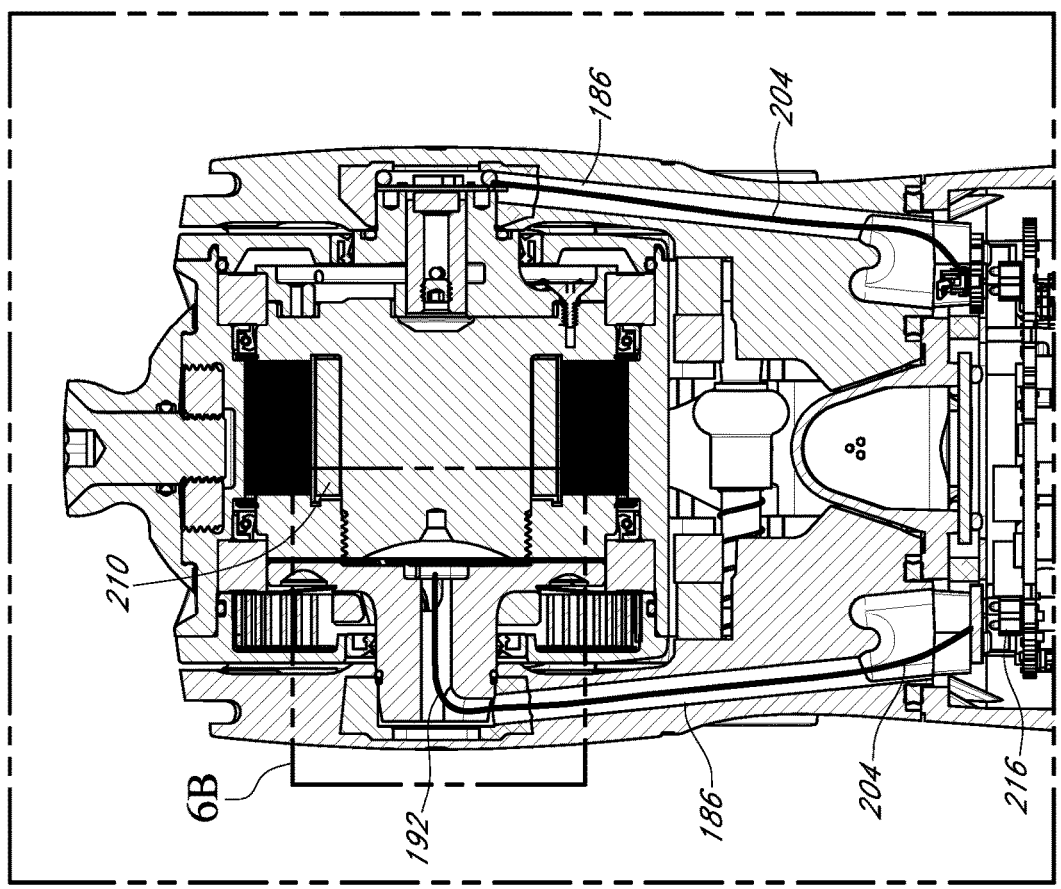
FIG. 6C is a cross-sectional view of an upper portion of the prosthetic knee assembly of FIG. 3.
Figure 6B:
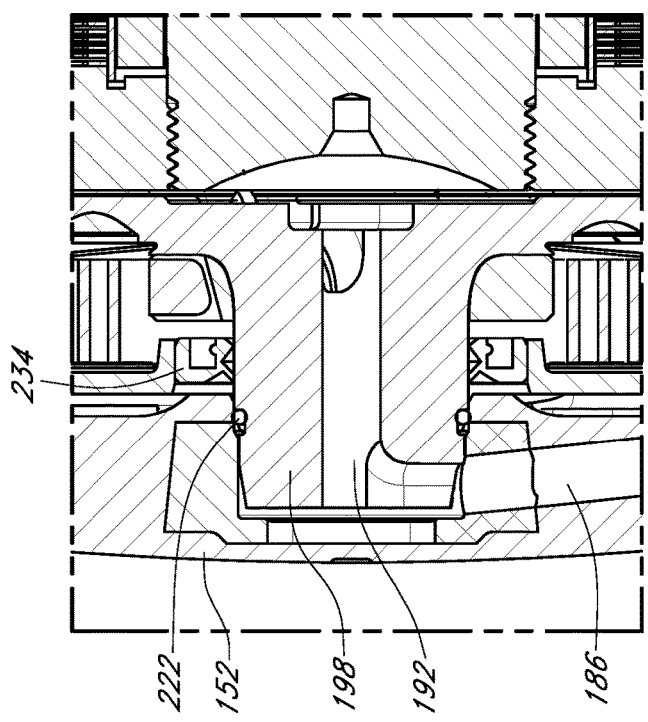
FIG. 6B is cross-sectional view of a side portion of a magnetorheological actuator of the prosthetic knee assembly of FIG. 3.

FIGS. 6A-6C depict various features relating to waterproofing the prosthetic knee. FIG. 6A depicts a close-up view of the top connector pyramid 132. The connector pyramid 132 can have drainage features. For example, the connector pyramid can have slots 180. The slots 180 can be suitable for providing drainage to a joint that incorporates the connector pyramid 132. The slots 180 may be spaced circumferentially around the connector pyramid 132. In some cases, the slots may be equally spaced. The connector pyramid 132 may have 1, 2, 3, 4, or more slots 180. Optionally, the slots 180 can extend linearly. In some cases, a bottom pyramid connector 138 may have features similar to those discussed with respect to the top connector pyramid 132.

FIG. 6B depicts a close-up view of a side mount 152 and surrounding structures. FIG. 6C depicts a cross-sectional view of the knee actuator 112 and other components. The side mount 152 can have a channel 186. The channel 186 can be an internal channel disposed within the side mount 152. The channel 186 cooperates with a channel 192 disposed within an actuator shaft 198. The channel 186 can be disposed between the electronic assembly 114 and the actuator shaft 198. The channel 186 can communicate with the channel 192. The channel 192 can be an axially aligned passage through the actuator shaft 192. Both channel 186 and 192 can have circular cross-section, although other cross-sections are also possible. The cooperating channels 186 and 192 can form a continuous path from the electronic assembly 114 to the interior of the actuator shaft 198. Electrical wiring 204 can be routed through the channels 186 and 192. The electrical wiring 204 can be coupled to the electronic assembly 114 and to the knee actuator 112 (e.g., the electromagnet 210). Enclosing the wiring 204 in the channels 186 and 192 can be advantageous to protect the electrical wiring 204 from damage (e.g., while the actuator shaft 198 and the knee actuator 112 rotate about their axis). In some embodiments, the wiring 204 can be coupled to the electronic assembly 114 via spring pins 216.

A watertight seal can be provided between the side mount 152 and the actuator shaft 198 by one or more side mount O-rings 222. The O-ring(s) 222 can be disposed between the side mount 152 and the actuator shaft 198. The actuator shaft 198 is sealed for water ingress via the O-ring(s) 222 in combination with dynamic seals 234.

Figure 7A:
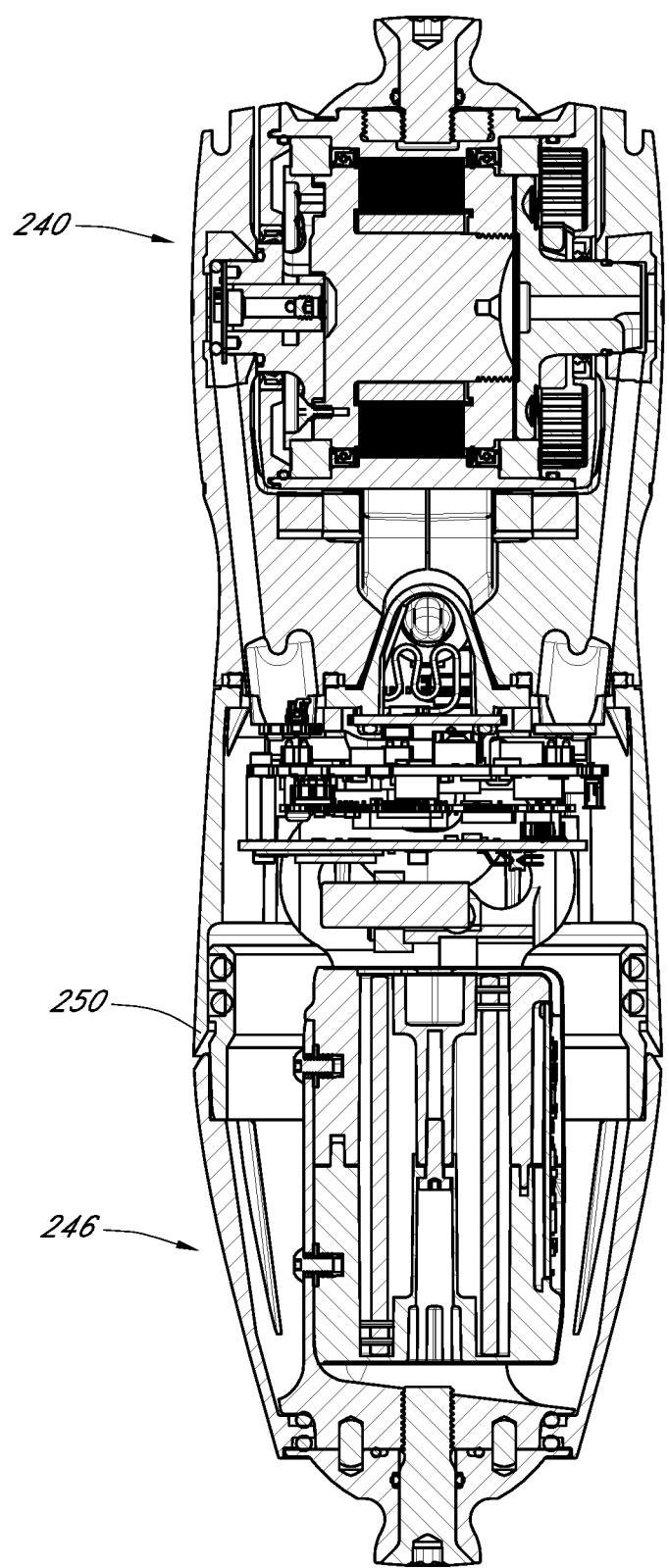
FIG. 7A is a cross-sectional view of the prosthetic knee assembly of FIG. 3.
Figure 7B:
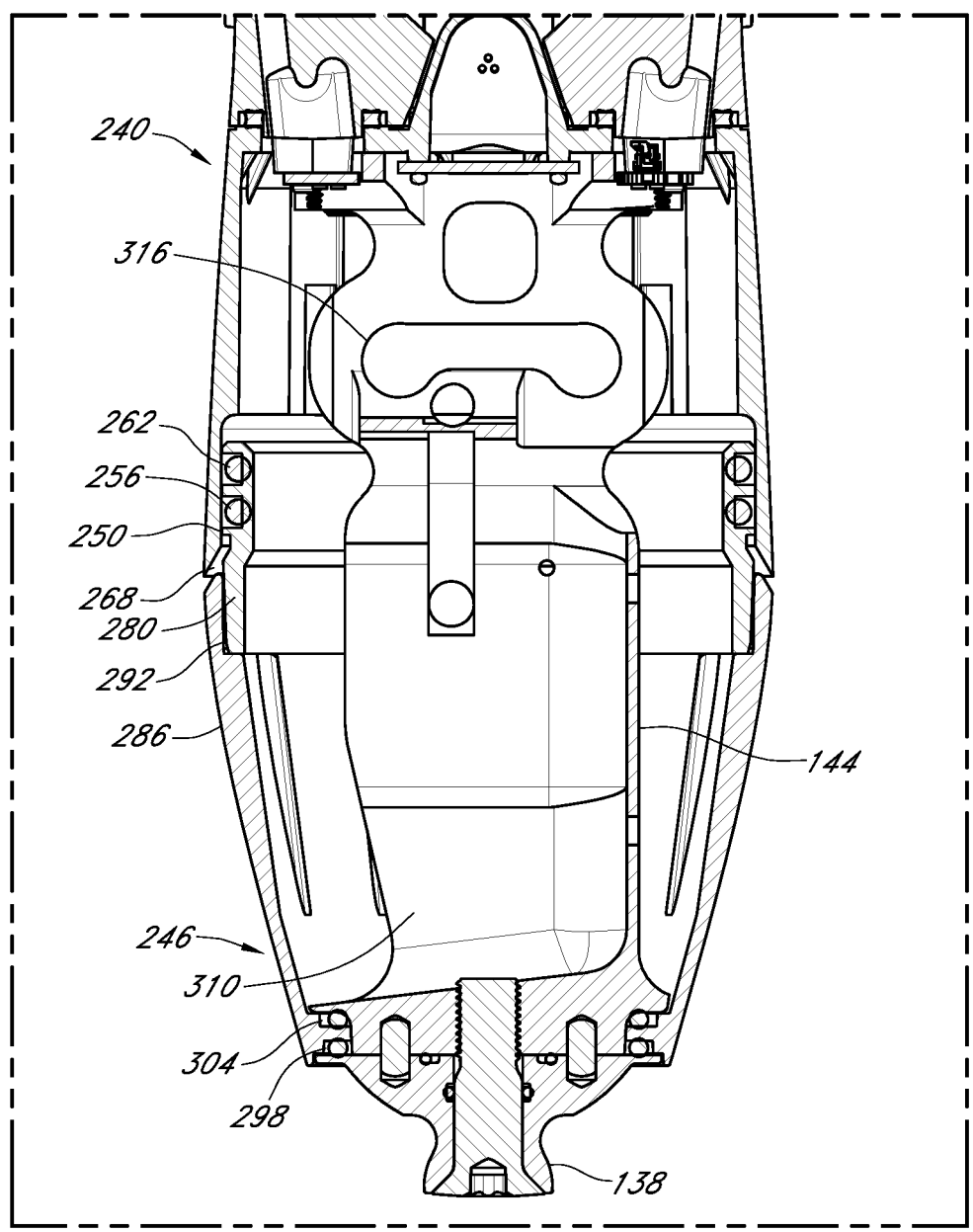
FIG. 7B is a cross-sectional view of a distal portion of the prosthetic knee assembly of FIG. 3.

FIGS. 7A and 7B depict a cross-sectional view of the prosthetic knee 110. The waterproof compartment 162 can be formed from two or more housings 240, 246. The housings 240, 246 can be a top or upper housing 240 and a lower housing 246 joined at a middle joint 250. The middle joint 250 can be sealed with one or more O-rings. In the depicted embodiment, the middle joint 250 is sealed with a lower O-ring 256 and an upper O-ring 262. The top housing 240 (e.g., which includes the upper enclosure 120) and the lower housing 246 can overlap such that either the top housing 240 is at least partially inserted into the lower housing 246, or such that the lower housing 246 is at least partially inserted into the top housing 240. For example, the lower housing 246 can be sized and shaped to at least partially fit inside the upper housing 240. The bottom portion of the top housing 240 can be sized to snugly fit around at least a portion of the top portion of the lower housing 246. The overlapping portions of the top housing 240 and the lower housing 246 may define the middle joint. The inset seam 268 can be a circumferential slot extending at an angle towards a distal end of the prosthetic knee 110. The upper and lower O-rings 256, 262 can positioned between the top housing 240 and the lower housing 246. The O-rings 256, 262 can be positioned around an outer surface of the lower housing 246. The O-rings 256, 262 can be positioned around an inner surface of the top housing 240. The lower housing 246 can have a middle portion 280 and a lower portion 286. In the depicted embodiment, the middle portion 280 is a separate piece that can fit inside the top housing 240 as described above. The middle portion 280 can fit snugly into the lower portion 286. The middle portion 280 can be fixedly attached to the lower portion 286. This fixed attachment can be waterproof. The attachment between the middle portion 280 and the lower portion 286 can be achieved through gluing the portions 280,286 together. For example, the middle portion 280 and lower portion 286 can be glued together at the seam 292. In some embodiments, the portions 280 and 286 are molded as a single piece (e.g., a monolithic piece, a seamless piece).

As depicted, the bottom pyramid connector 138 can be sealed, with a watertight seal, to the lower housing 246. The watertight seal can use O-rings 298 and 304. In some embodiments, the O-ring 298 can be positioned between the pyramid connector 138 and the lower bottle housing 246. The O-ring 304 can be positioned between the load cell frame 310 and the lower bottle housing 246. The load cell frame 310 and the sensing element 316 can be utilized by the prosthetic knee to measure axial forces and anterior-posterior moments.

Sealing the top housing 240 and the lower housing 246 together results in a single waterproof compartment 162. A single waterproof compartment 162 is advantageous al least because it reduces the complexity associated with sealing of wires (e.g., wires 204).

In some embodiments, the top housing 240 and the lower housing 246 can move (e.g., move or slide axially) relative to each other. The relative motion may be caused by loading on the knee. The translation between the top housing 240 and the lower housing 246 can be in the range of about 0.5 mm to 2 mm. The prosthetic knee 110 may, during normal walking, cause about a 0.5 mm relative motion between the top housing 240 and the lower housing 246. The prosthetic knee 110 may, during extreme loading, cause about a 2 mm relative motion between the top housing 240 and lower housing 246. The O-rings 256, 262 may be selected such that normal walking causes about a 0.5 mm relative motion between the top housing 240 and the lower housing 246. The relative motion can be tilting, translating, or any combination of the two. The O-rings 256, 262 may be selected such that extreme loading causes about a 2.0 mm relative motion between the top housing 240 and lower housing 246. Extreme loading can occur during toe-off event. Extreme loading can be loading around or exceeding 600 Nm. The material and size of the O-rings 256, 262 can be selected to maintain a watertight seal between the top housing 240 and the lower housing 246. The O-rings 256, 262 allow the top housing 240 and lower housing 246 to move (e.g., slide) relative to each other thereby preventing force transmission via the top and lower housings 240, 246 to inhibit (e.g., prevent) the effect on load cell measurements by the sensing element 316. The O-rings 256, 262 can reduce the effect of thermal stress, caused by expansion/contraction of the housing, on load cell measurements by the sensing element 316.

B. Outer Cover for Prosthetic Knee

Figure 8:
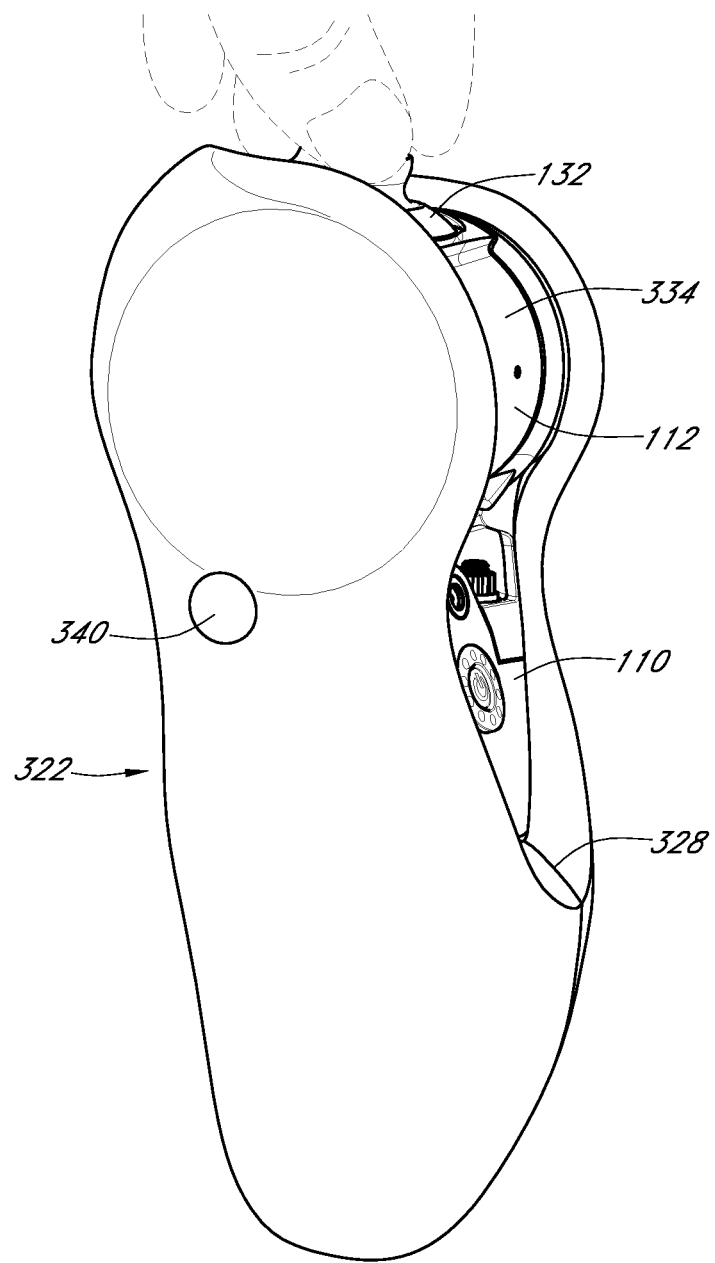
FIG. 8 is a perspective view of a prosthetic knee with an outer cover attached thereto.

FIG. 8 depicts an outer cover 322 mounted on a prosthetic knee 110. The outer cover 322 can releasably couple to (e.g., extend over at least a portion of) the prosthetic knee 110 (e.g., over the upper enclosure 120 and lower enclosure 126, over the top or upper housing 240 and lower housing 246). The outer cover 322 covers a majority of the outer surface of the waterproof compartment 162. The outer cover can have a closing interface 328. The closing interface 328 can run approximately longitudinally along the rear of the outer cover 322. The outer cover 322 can include a cutout 334. The cutout 334 can be disposed on the rear of the outer cover 322. The cutout 334 can extend to the top of the actuator 112 and can include the area around the top pyramid connector 132. The material of the outer cover 322 can be a closed cell foam material. For example, the material of the outer cover 322 may be ethylene-vinyl acetate. It is advantageous for the material to be lightweight.

The outer cover 322 can include a toggle cover portion 340. The toggle cover portion 340 can allow a user to know by visual inspection the status of the position lock control 150. The toggle cover portion 340 is also functional to allow a user to toggle the position lock control 150. The toggle cover portion 340 can have flexible extending thin sections.

Figure 9A:
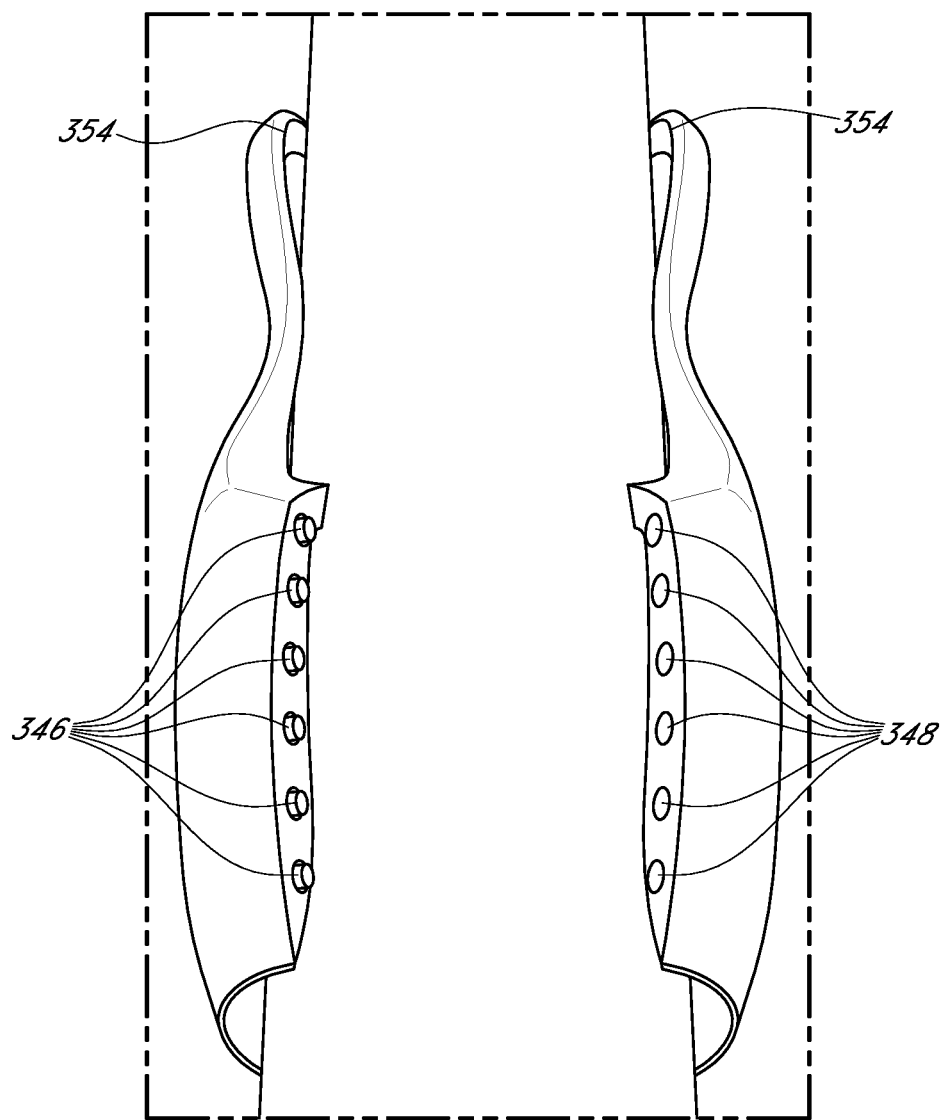
FIG. 9A is a perspective view of an outer cover for a prosthetic knee in an open position.
Figure 9B:
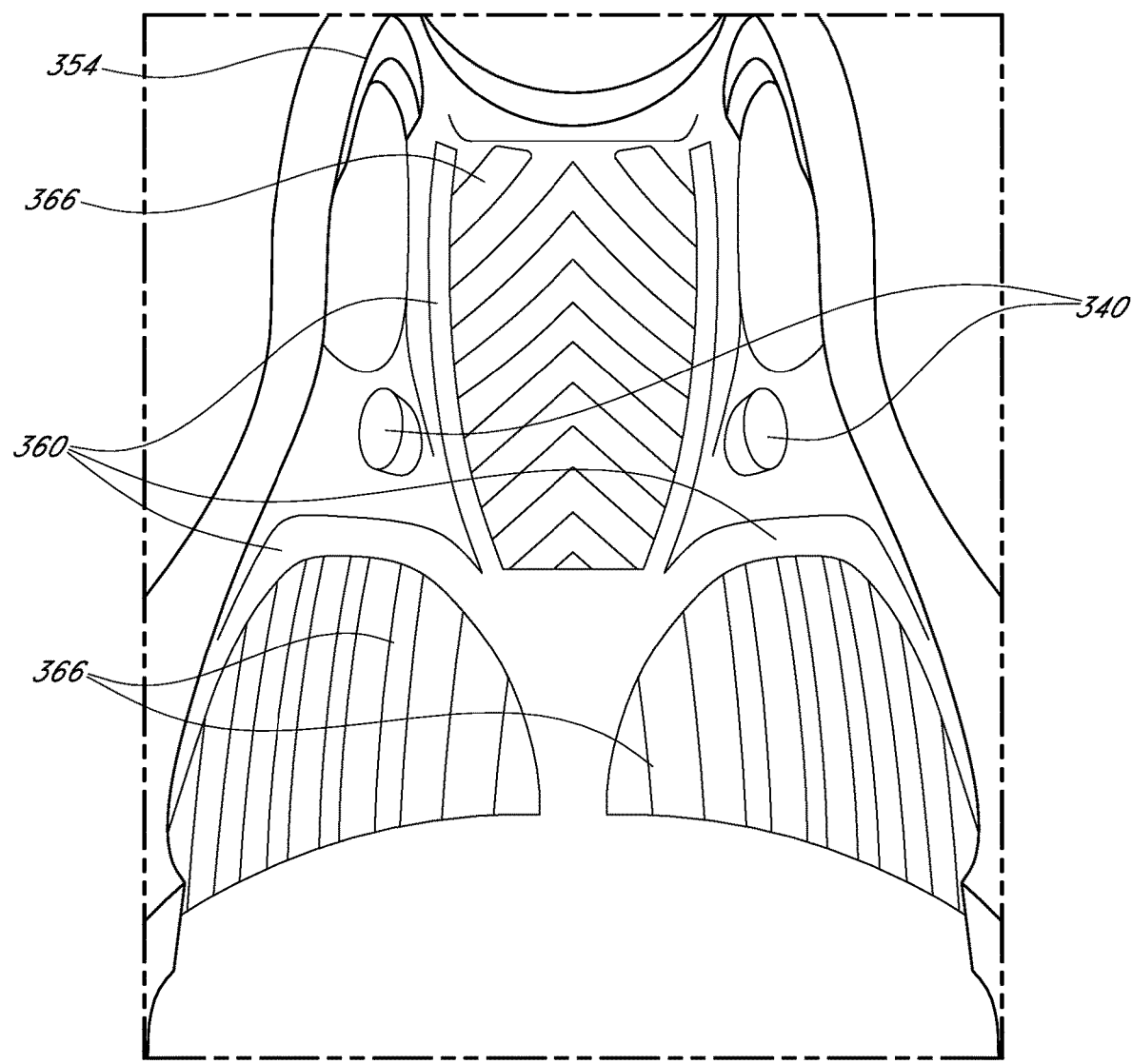
FIG. 9B is a perspective view of an upper portion of an inner surface of an outer cover for a prosthetic knee.

FIGS. 9A and 9B depict the outer cover 322 without the prosthetic knee 110. FIG. 9A depicts the outer cover 322 with the closing interface 328 opened, decoupled and/or unlocked. The closing interface 328 can be easily opened. In the depicted embodiment, the closing interface 328 is held closed by a series of left and right magnets 346, 348. The series of left and right magnets 346, 348 can be positioned on the edge of the closing interface. In some embodiments, the left magnets 346 can all have the same polarity orientation. For example, the left magnets can all have their north poles facing towards the right magnets 348. In another embodiment, the left magnets 346 could have an alternating polarity orientation. For example, the left magnets 346 can have alternating north and south poles facing towards the right magnets 348. The orientation of the right magnets 348 can be opposite the orientation of the left magnets 346 to facilitate a magnetic attractive force between the left and right magnets 346, 348. The magnetic attractive force can tend to close the interface 328. There can be 1, 2, 3, 4, 5, 6, 7, 8, 9, 10, or other numbers of pairs of left and right magnets 346, 348. The magnets 346, 348 can be any suitable type of magnet. The magnets 346, 348 can be a variety of shapes. For example, the magnets 346, 348 can be tulip-shaped, circular, rectangular, oval, or another shapes. Tulip-shaped can refer to cylindrical magnets with two or more different diameters. In some embodiments, the magnet could be a magnetic strip. The left magnets 346 can protrude and can at least partially fit into inset or recessed portions containing the right magnets 348 on the right hand side. Alternatively, the right magnets 348 can protrude, and can at least partially fit into inset portions containing left magnets 346 on the left-hand side. In still another implementation, the left magnets 346 can include one or more magnets that protrude as well as one or more inset or recessed magnets that can engage corresponding one or more magnets of the right magnets 348 that are inset or recessed and one or more magnets that protrude, respectively. The magnets can hold the left and right sides of the interface 328 flush to each other when the interface 328 is closed. In an alternative, a zipper, or other mechanical fastening system could be used instead of the magnets 346, 348.

The outer cover 322 has a top edge 354 (e.g., on a left side and a right side of the outer cover 322) that can mate with the grooves 156 of the side mounts 152 to advantageously facilitate securing of the cover 322 on the upper enclosure 120. Contours 360 can at least partially mesh with features on the prosthetic knee 110. The top edge 354 and the contours 360 can hold the cover 322 on the prosthetic knee 110. The combination of the closing interface 328, the grooves 156 and the contours 360 can hold the cover 322 in place relative to the prosthetic knee 110 (e.g., relative to the upper or top housing 240 and the lower housing 246). The outer cover 322 has drainage canals 366 on the interior surface. The outer cover 322 may not have a watertight seal to the prosthetic knee 110. The drainage canals 366 can allow water to drain from between the prosthetic knee 110 and the cover 322.

Figure 10A:
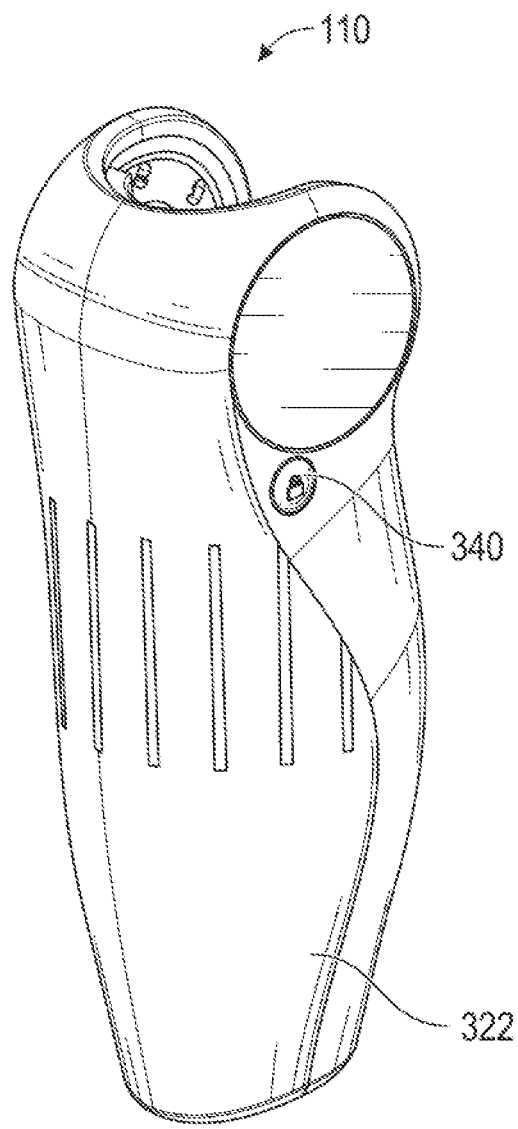
FIGS. 10A and 10B are various perspective views of a portion of a prosthetic knee with an outer cover attached.
Figure 10B:
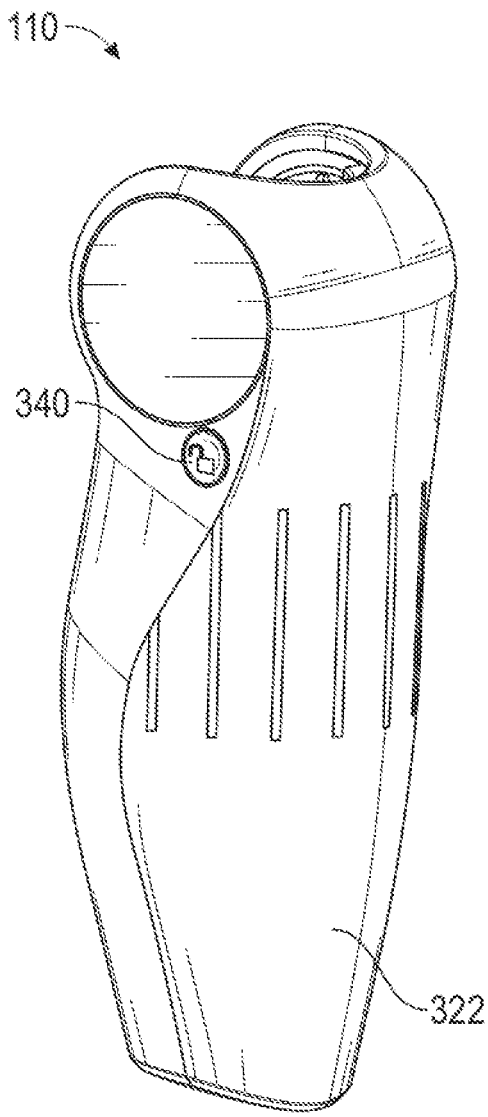
Figure 11:
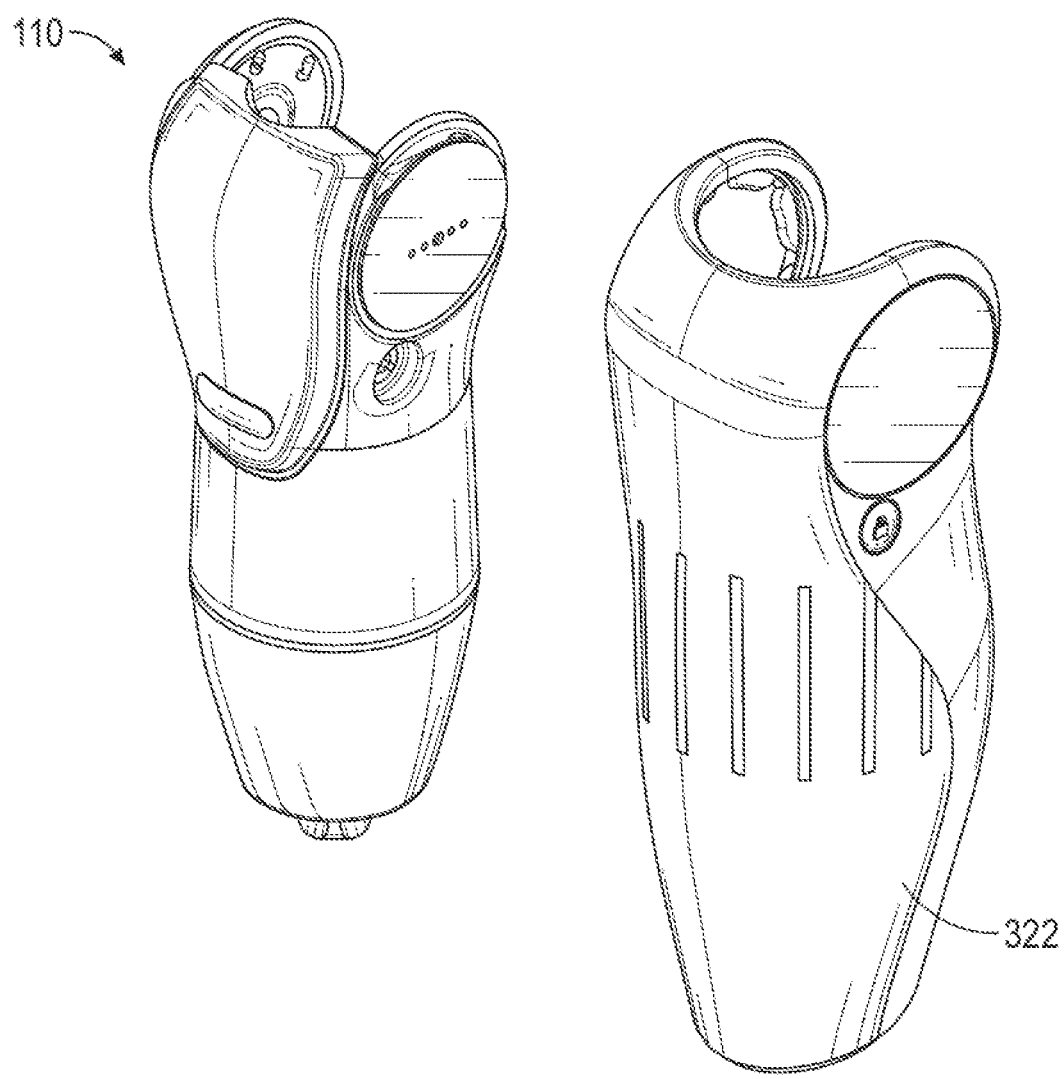
FIG. 11 is a perspective view of the prosthetic knee portion of FIGS. 10A and 10B with the outer cover detached from the prosthetic knee.

FIGS. 10A and 10B illustrate various perspective view of another implementation of the prosthetic knee 110 with the outer cover 322, where an upper portion of the prosthetic knee (e.g., pyramid, actuator) is excluded to show features of how the prosthetic knee 110 couples to the outer cover 322. As described herein, the outer cover 322 can include a toggle cover portion 340 (e.g., button cover). The toggle cover portion 340 can be positioned over (for example, positioned on top of) the position lock control 150 of the prosthetic knee 110. In some implementations, the prosthetic knee 110 can include a separate position lock button and a separate position unlock button, and the cover 322 can include separate toggle cover portions 340 that correspond to the position lock button and the position unlock button (e.g., on left and right sides of the outer cover 322). As such, a user can actuate the position lock button and the position unlock button to lock or unlock the position of the prosthetic knee 110 (e.g., the position of the knee actuator 112). In another implementation, the same button can be used for locking and unlocking the position of the prosthetic knee 110 (e.g., the position lock control 150 described herein), which can be actuated in a push-push mode to lock and unlock the prosthetic knee 110. FIG. 11 illustrates a perspective view of the outer cover 322 and a portion of the prosthetic knee 110 without the outer cover 322.

Figure 12A:
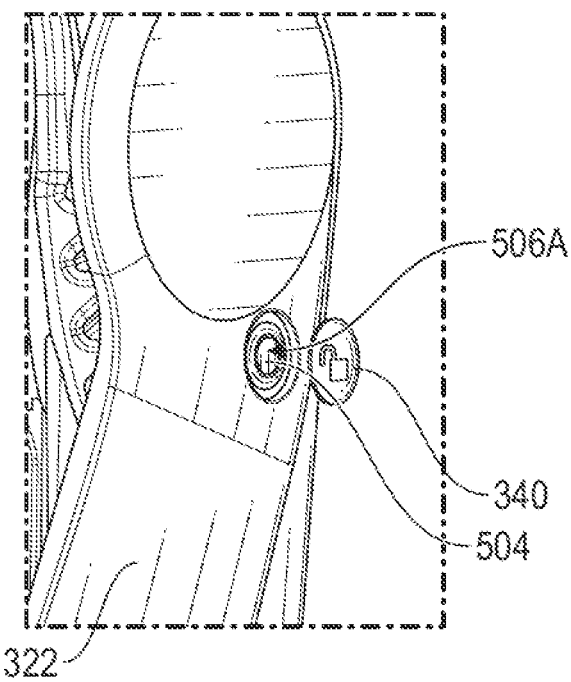
FIG. 12A is an enlarged, perspective view of a portion of the outer cover of FIGS. 10A and 10B illustrating a toggle cover.
Figure 12B:
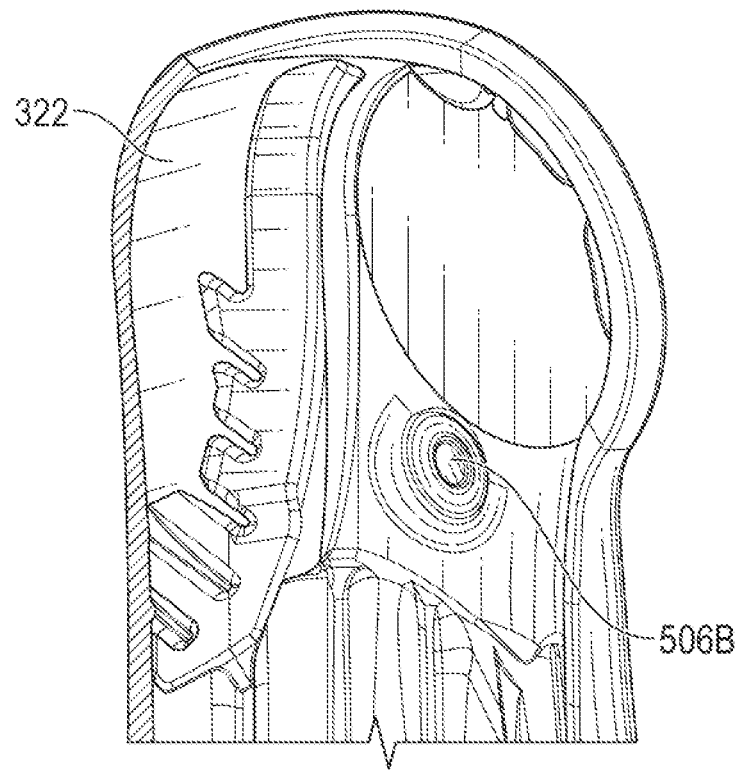
FIG. 12B is an enlarged, perspective view of an inside portion of the outer cover of FIGS. 10A and 10B.
Figure 13:
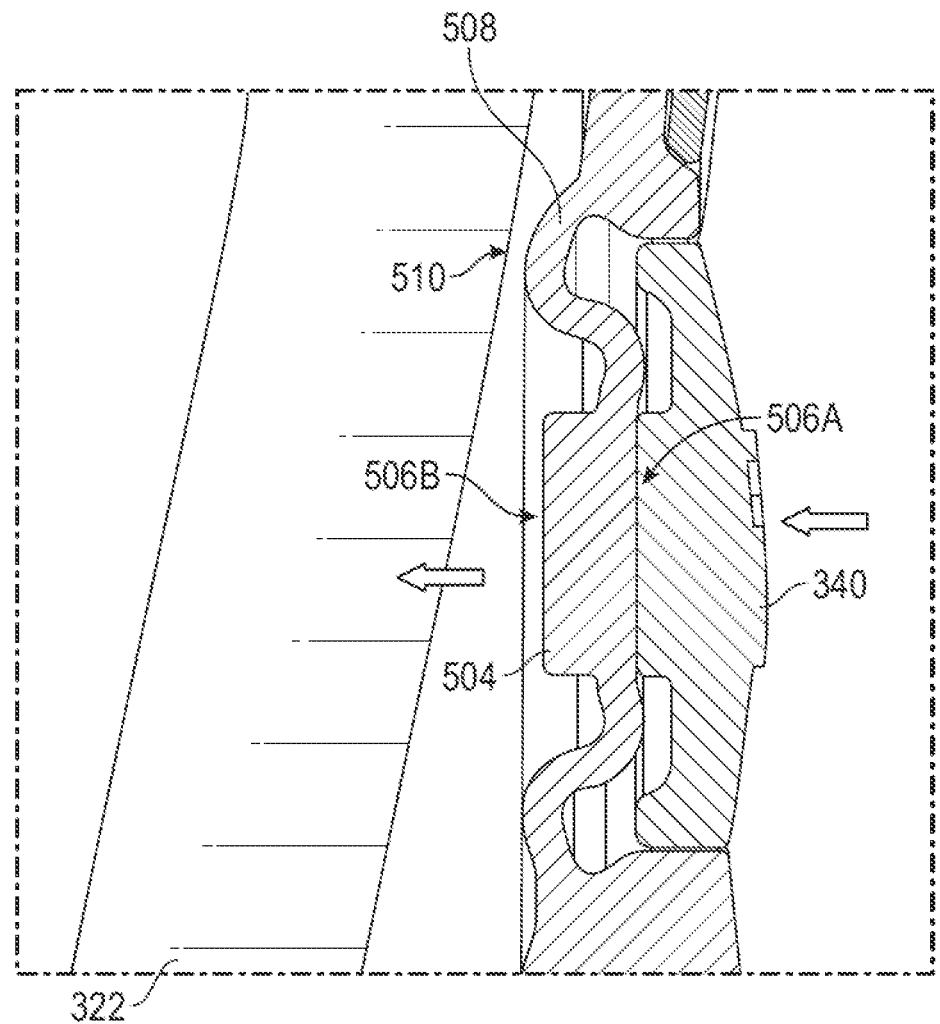
FIG. 13 is an enlarged, cross-sectional view of the toggle cover of FIG. 12A.

With reference to FIGS. 12A, 12B, and 13, the outer cover 322 can include a button 504 with an outer surface 506A and an inner surface 506B. The toggle cover portion 340 (e.g., button cover) can be positioned on top (e.g., abut against the outer surface 506A) of the button 504. In some examples, the toggle cover portion 340 is a separate part that is attached (e.g., via an adhesive) to the outer surface 506A of the button 504. Alternatively, the toggle cover portion 340 can be integrated (e.g., one piece, seamless, monolithic) with the button 504. The button 504 can be connected to the outer cover 322 via a flexible membrane 508, which can be circumferentially attached to the button 504. The flexible membrane 508 can include a flex portion 510 that can bias the button 504 to an unactuated position, while allowing resilient movement of the flexible membrane 508. In some implementations, the flexible membrane 508 is a thin membrane of ethylene-vinyl acetate (EVA). However, the flexible membrane 508 can be of other suitable (e.g., flexible, resilient) materials.

FIG. 13 shows the flexible membrane 508 in an unactuated state. When unactuated (e.g., not pressed inward in a direction indicated by arrows in FIG. 13), the flex portion 510 can extend away from the cover 322 and bend towards the toggle cover portion 340. When the button 504 is actuated (e.g., pushed inward in a direction indicated by arrows in FIG. 13 by a user pressing on the toggle cover portion 340), the flex portion 510 of the flexible membrane 508 can flex inward (for example, in a direction indicated by arrows in FIG. 13) and allow the button 504 to move inward relative to an inner surface of the outer cover 322 to engage and actuate the position lock control 150 as described above to lock or unlock the prosthetic knee 110.

Figure 14A:
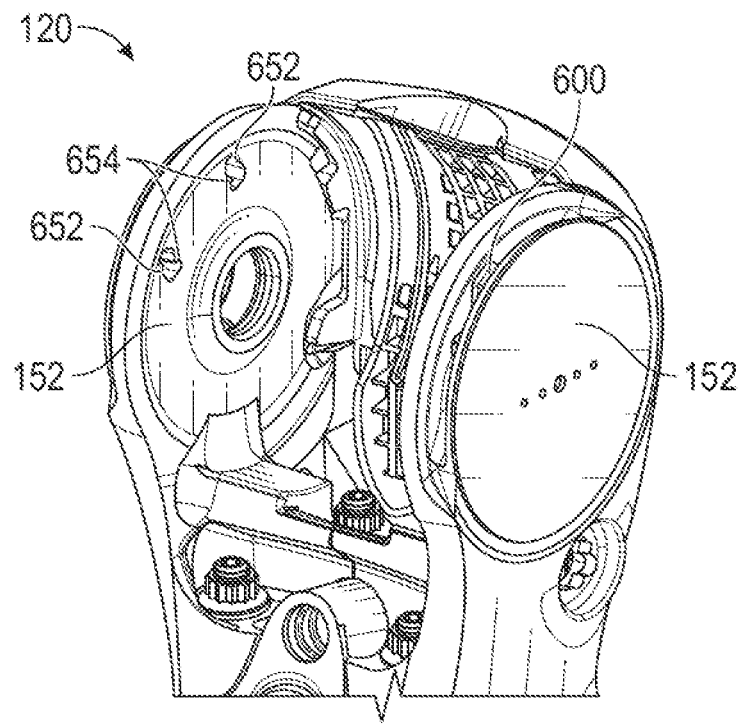
FIGS. 14A and 14B are various views of an upper portion of a prosthetic knee without a cover.
Figure 14B:
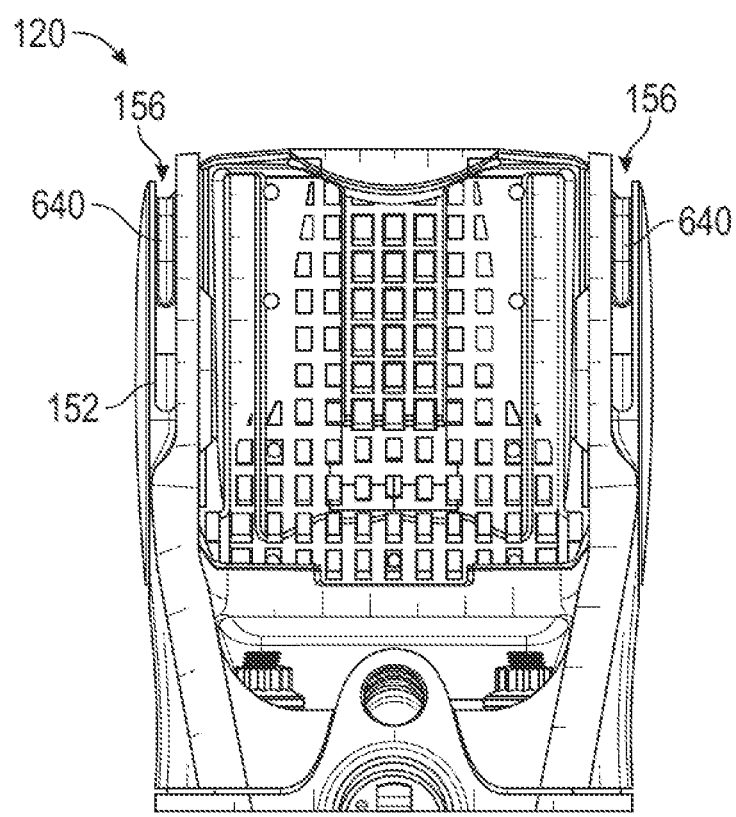

FIGS. 14A and 14B illustrate various views of another implementation of the upper enclosure 120 of the prosthetic knee 110, where an upper portion of the prosthetic knee 110 (e.g., actuator, pyramid) is excluded to show features of how the prosthetic knee 110 couples to the outer cover 322. As shown in FIG. 14B and described herein, the upper enclosure 120 can include a set of grooves 156 formed behind the side mounts 152. For example, one groove 156 can be positioned on a medial side of the upper enclosure 120 while another groove 156 can be positioned on a lateral side of the upper enclosure 120. An adaptor 640 can be positioned (e.g., removably positioned) in the groove 156. The adaptor 640 can be fixedly positioned within the groove 156 and can include one or more alignment features to allow a corresponding outer cover 322 to be properly mounted to the prosthetic knee 110 via the grooves 156, as further discussed below. The side mount 152 can include slots 652 formed on an inner side (for example, the side facing away from the groove 156) of the side mount 152 and extending into the grooves 156. The slots 652 can lockingly engage legs 650 of the adaptor 640 (see FIGS. 16A and 16B) to lock the adaptor 640 within the groove 156. The slot 652 can include a cutout 654 formed at an angle with respect to the rest of the slot 652. For example, the cutout 654 can be formed at about 90 degrees with respect to the rest of the slot 652.

Figure 15A:
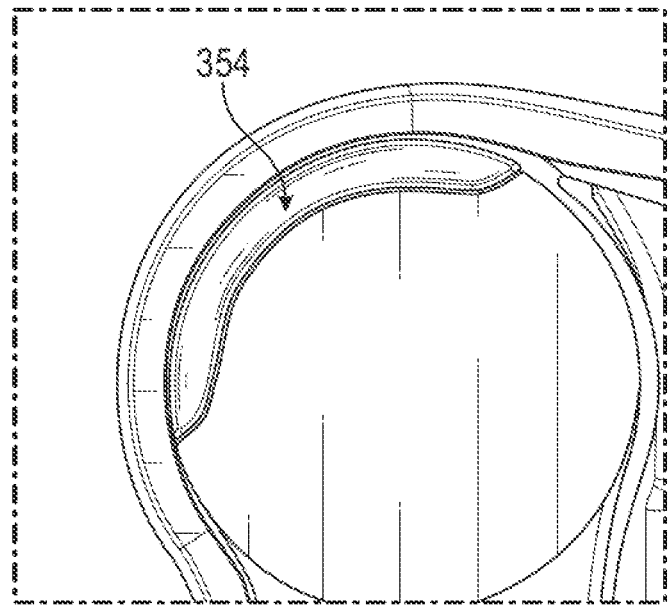
FIGS. 15A, 15B, and 15C illustrate various embodiments of a top edge of an outer cover for a prosthetic knee.
Figure 15B:
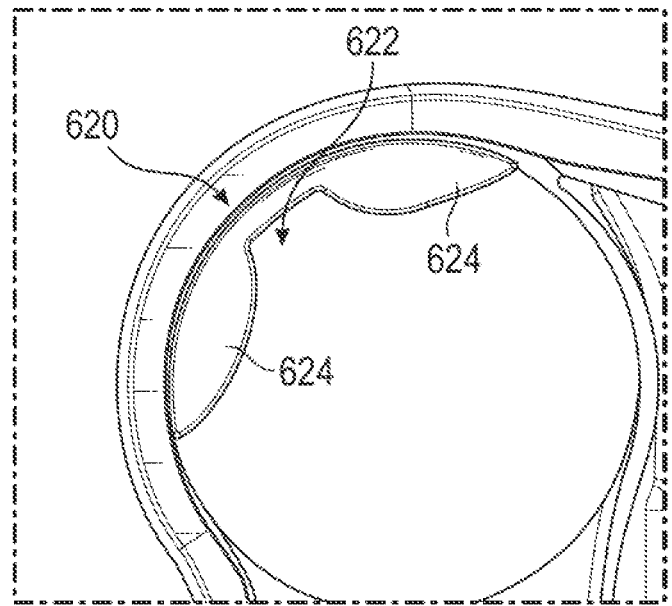
Figure 15C:
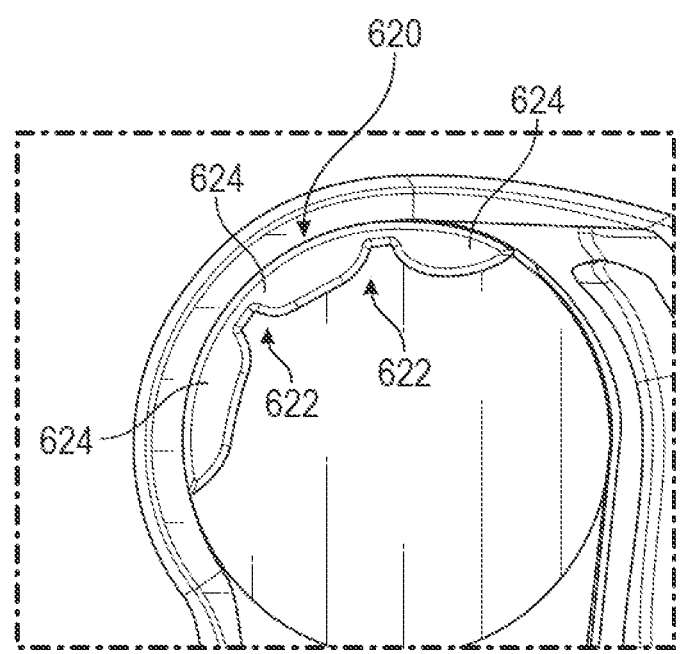

FIGS. 15A, 15B, and 15C illustrate various implementations of the outer cover 322. FIG. 15A illustrates the outer cover 322 with the top edge 354 (see FIGS. 9A and 9B) that does not comprise any cutouts (e.g., the top edge 354 is a single continuous edge). The top edge 354 (or a lip) can have a contour that closely mirrors (for example, corresponds) to that of the groove 156 without an adaptor (for example, the adaptor 640). FIG. 15B illustrates the outer cover 322 with a top edge 620. The top edge 620 can include a recess 622 formed between adjacent flaps 624 (e.g., the top edge 620 has two flaps 624 separated by the recess 622). FIG. 15C illustrates the outer cover 322 with another embodiment of the top edge 620 that can include two recesses 622 formed between the flaps 624 (e.g., the top edge 620 has three flaps 624, each pair of flaps 624 separated by a recess 622). The flaps 624 may have a circular or smooth rounded contour. Alternatively, the flaps 624 may have an angled contour. Additionally or optionally, the recess 622 can include a circular or rounded contour. Alternatively, the recess 622 can include an angled contour.

Figure 16A:
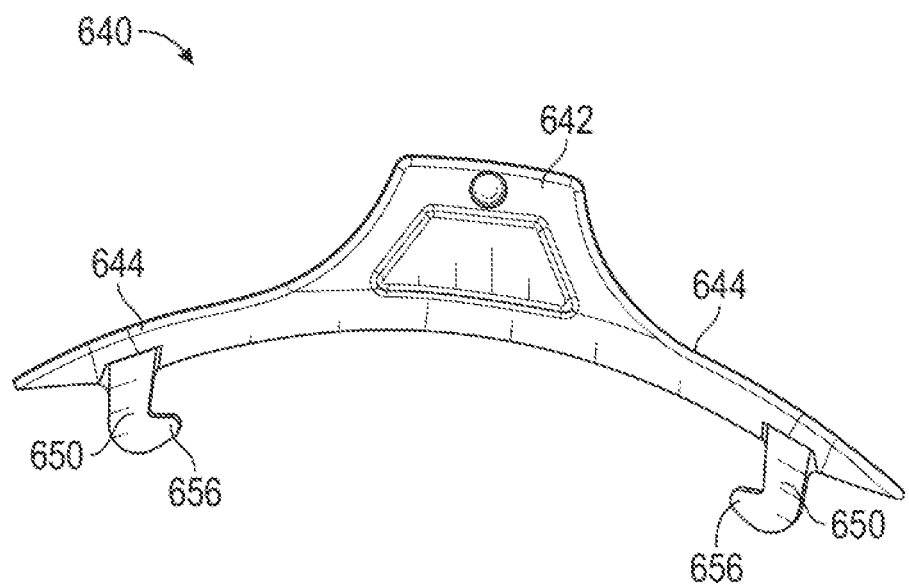
FIGS. 16A and 16B illustrate various embodiments of a coupling device for a prosthetic knee to couple with an outer cover.
Figure 16B:
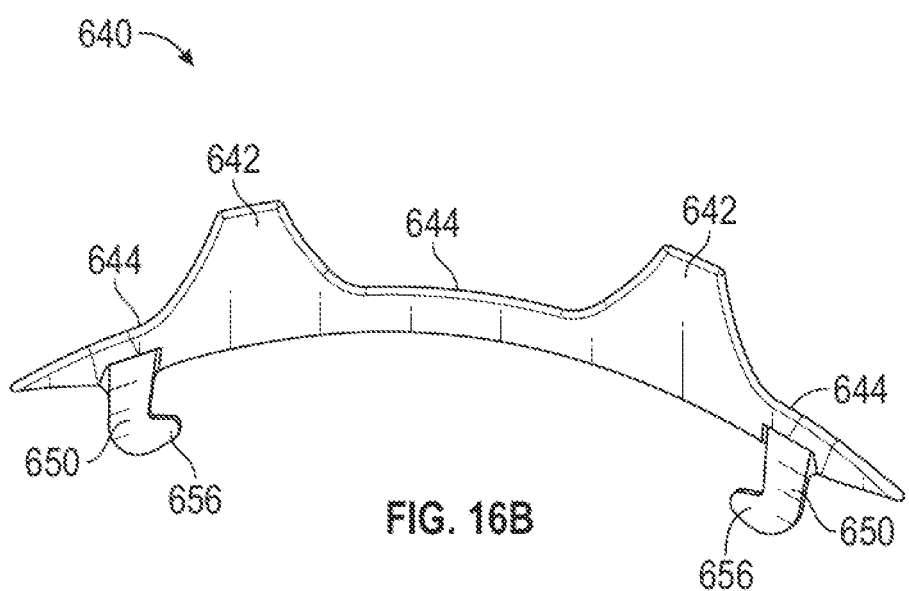

FIG. 16A illustrates the adaptor 640. The adaptor 640 can include a protrusion 642 (e.g., tooth-like or gear-like protrusion) that extends (e.g., protrude) relative to a curved lower portion 644. FIG. 16B illustrates another embodiment of the adaptor 640 that includes, for example, two protrusions 642 (e.g., tooth-like or gear-like protrusion), each extending (e.g., protruding) relative to a curved lower portion 644. The shapes or contours of the recesses 622 and the flaps 624 of the top edge 620 can correspond to (e.g., approximate, be substantially similar to) the shapes of the protrusions 642 and the lower portion 644 of the adaptor 640, respectively. Advantageously, the protrusions 642 are located in different locations relative to the lower portion 644 for the adaptor 640, such that once coupled in the grooves 156 the adaptor 640 allow only a correspondingly shaped outer cover 322 to be coupled to the prosthetic knee 110, as discussed below.

The adaptor 640 can include legs 650 that extend from an underside of the lower portion 644 and are dimensioned and shaped to fit into (e.g., extend at least partially into) the slots 652. The legs 650 can include a detent 656 that can be dimensioned and shaped to fit in (e.g., at least partially extend into) the slots 652 and the cutouts 654 of the slot 652. Once inserted into the cutout 654, the detent 656 of the legs 650 can inhibit (e.g., prevent) the removal of the adaptor 640 from the groove 156. The adaptor 640 can be inserted into the groove 156 such that the legs 650 are inserted into the slots 652 formed on the side mount 152. As described herein, the cutout 654 of the slot 652 can, for example, lockingly receive the legs 650 and/or the detent 656 of the legs 650 to lockingly position the adaptor 640 within the groove 156.

Figure 17A:
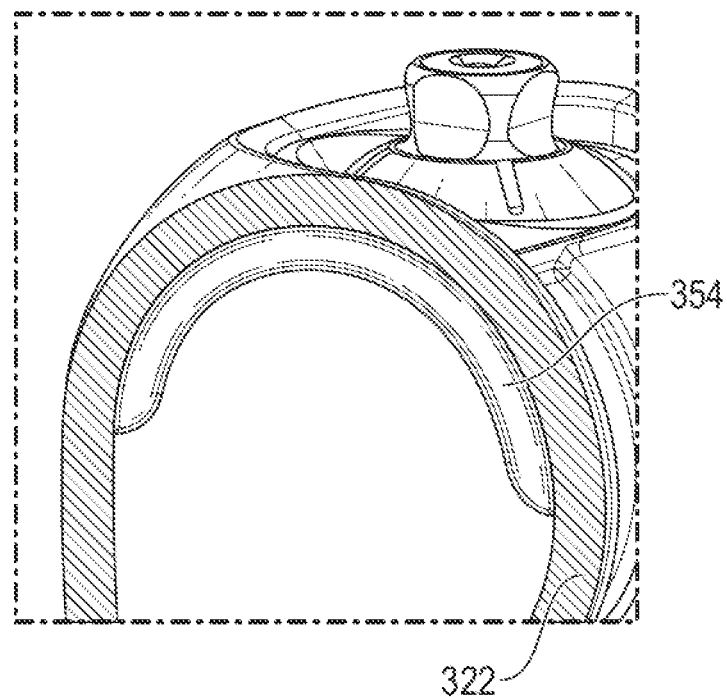
FIGS. 17A, 17B, and 17C illustrate coupling between various embodiments of a top edge of a cover and various embodiments of a coupling device for a prosthetic knee.
Figure 17B:
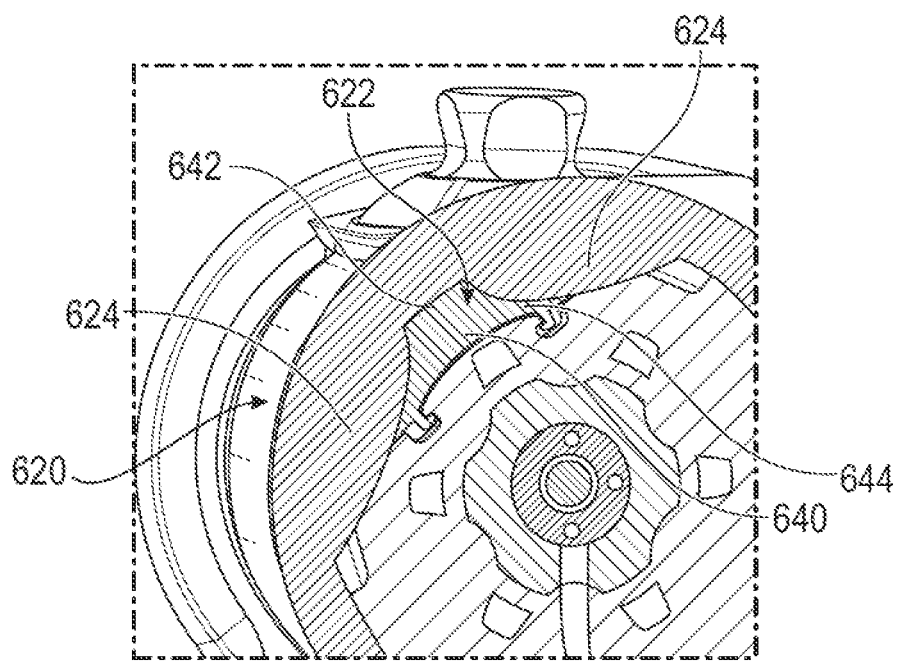
Figure 17C:
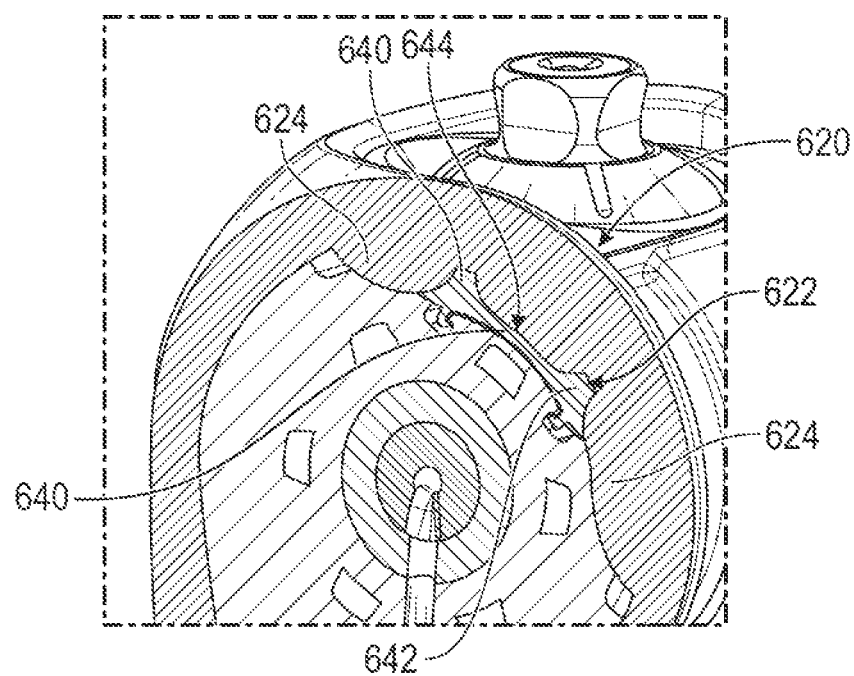

With reference to FIGS. 17A, 17B, and 17C, the shape or contour of the adaptor 640 can correspond with a particular outer cover 322 that can be coupled with the prosthetic knee 110. For example, since the top edge 620 of the outer cover 322 shown in FIG. 17B includes one recess 622, this outer cover 322 with the top edge 620 can mate with the adaptor 640 shown in FIG. 16A. Likewise, since the outer cover 322 with top edge 620 shown in FIG. 17C includes two recesses 622, the outer cover 322 with the top edge 620 shown in FIG. 15C can mate with the adaptor 640 shown in FIG. 16B. As such, if the grooves 156 of the upper enclosure 120 includes the adaptor 640 shown in FIG. 16A (with one protrusion or tooth 642), the outer cover 322 with the top edge 620 shown in FIG. 15B (with one recess 622) can be properly inserted into the groove 156, while the outer cover 322 with the top edge 620 shown in FIG. 15C (with two recesses 622) will not properly fit over the adaptor 640 in the groove 156. Similarly, if the grooves 156 of the upper enclosure 120 includes the adaptor 640 shown in FIG. 16B (with two protrusions or teeth 642), the outer cover 322 with the top edge 620 shown in FIG. 15C (with two recesses 622) can be properly inserted into the groove 156, while the outer cover 322 with the top edge 620 shown in FIG. 15B (with one recess 622) will not properly fit over the adaptor 640 shown in FIG. 16B in the groove 156.

It is contemplated that the shapes or contours of the adaptor 640, the recess(es) 622, the flaps 624, the protrusion(s) 642, and the lower portion 644 may be different from the illustrated implementations, and other shapes or contours may be utilized. The shapes or contours of the recess 622 can correspond to that of the protrusion 642, and the shapes or contours of the flap 624 can correspond to that of the lower portion 644. As such, the type of adaptor (for example, having a certain shape or contour) used for the groove 156 of the prosthetic knee 110 can determine what type of outer cover 322 can be used. Additionally, a different number of protrusions (for example, the protrusion 642), recesses (for example, the recess 622), flaps (for example, the flap 624), and lower portions (for example, the lower portion 644) may be utilized.

Although the adaptor 640 described herein include one or more the protrusions 642, it is contemplated that the adaptor 640 can instead include one or more recesses while the top edges 620 of the cover can include one or more protrusion that mate with the one or more recesses in the adaptors.

Figure 18B:
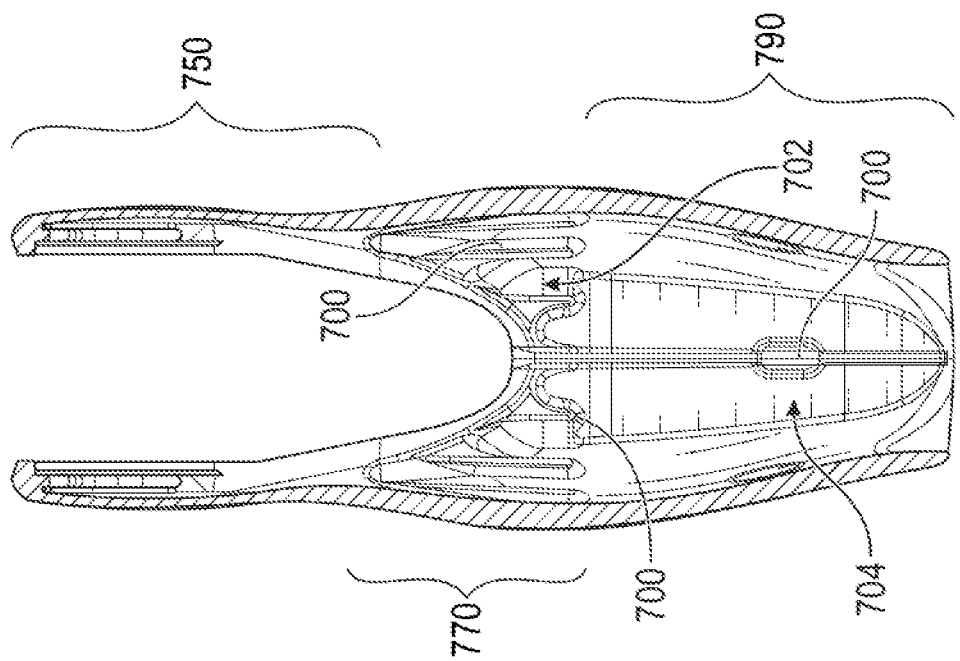
FIGS. 18A and 18B are cross-sectional views of an outer cover for a prosthetic knee.
Figure 18A:
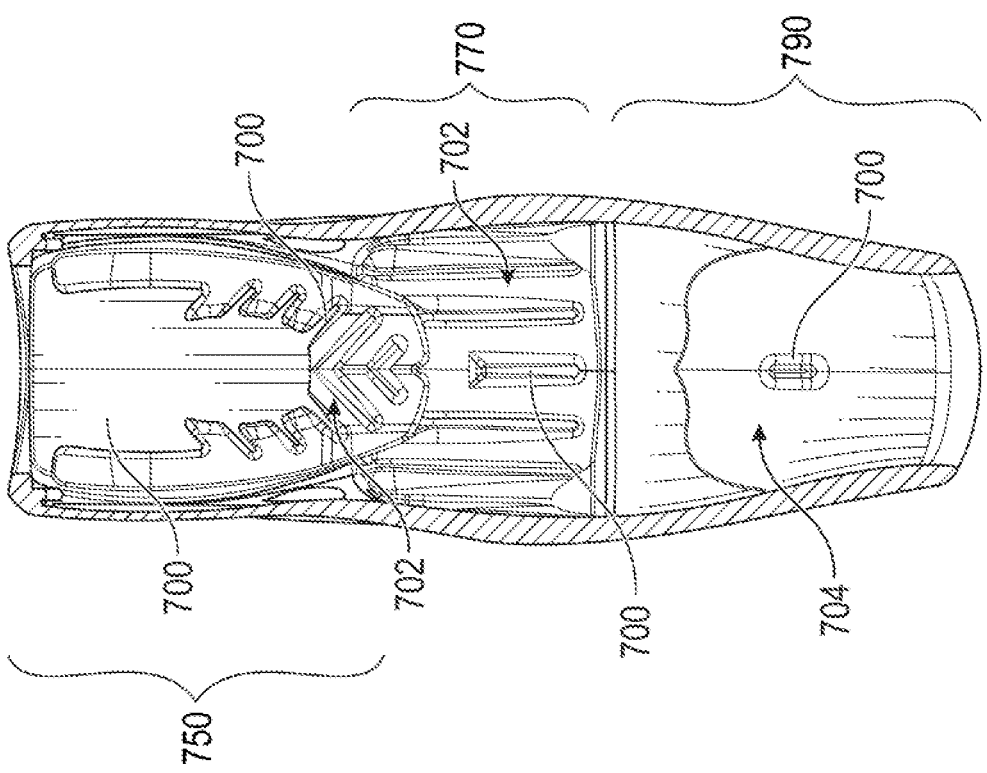

FIGS. 18A and 18B illustrate various cross-sectional view of an implementation of the outer cover 322. FIG. 18A illustrates a cross-sectional view of a front half of the outer cover 322, while FIG. 18B illustrates a cross-sectional view of a rear half of the outer cover 322. In the illustrated implementation, the outer cover 322 can include a number of raised portions 700 and a number of channels 702 (or cutouts) formed between raised portions 700. The channels 702 can be formed vertically or at an angle to facilitate flow of water between the outer cover 322 and the prosthetic knee 110 (e.g., between the outer cover 322 and the upper or top housing 240 and the lower housing 246). For example, a top portion 750 of the outer cover 322 can include the channels 702 formed at an angle, while a middle portion 770 of the outer cover 322 can include the channels 702 formed vertically. A bottom portion 790 of the outer cover 322 can include a clearance portion 704 that does not include any channels and can be positioned a predetermined distance away from the prosthetic knee 110 during use (e.g., the clearance portion 704 can be positioned farther apart from a surface of the prosthetic knee 110, facilitated by the raised portion 700 in the bottom portion 790, than the top portion 750 and/or middle portion 770 of the outer cover 322). The clearance portion 704 can further facilitate flow of water and prevent any water buildup between the outer cover 322 and the prosthetic knee 110.

FIGS. 19A-21 show a schematic view of an outer cover 322A. Some of the features of the outer cover 322A are similar to features of the outer cover 322 in FIGS. 1-18B. Thus, reference numerals used to designate the various features or components of the outer cover 322A are identical to those used for identifying the corresponding features of components of the outer cover 322 in FIGS. 1-18B, except that an "A" has been added to the numerical identifier. Therefore, the structure and description for the various features of the outer cover 322 and how it's operated in FIGS. 1-18B are understood to also apply to the corresponding features of the outer cover 322A in FIGS. 19A-21, except as described below.

Figure 19B:
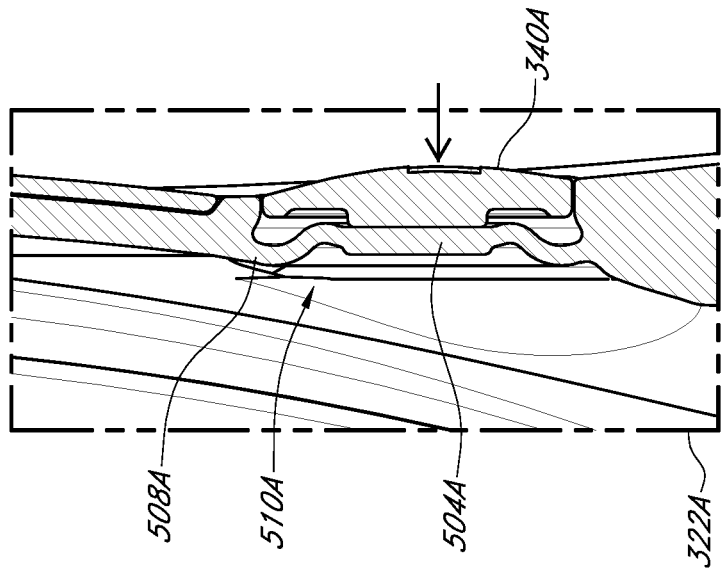
FIGS. 19A and 19B are cross-sectional views of a left side portion and a right-side portion of an outer cover illustrating toggle covers on the left and right sides of the outer cover.
Figure 19A:
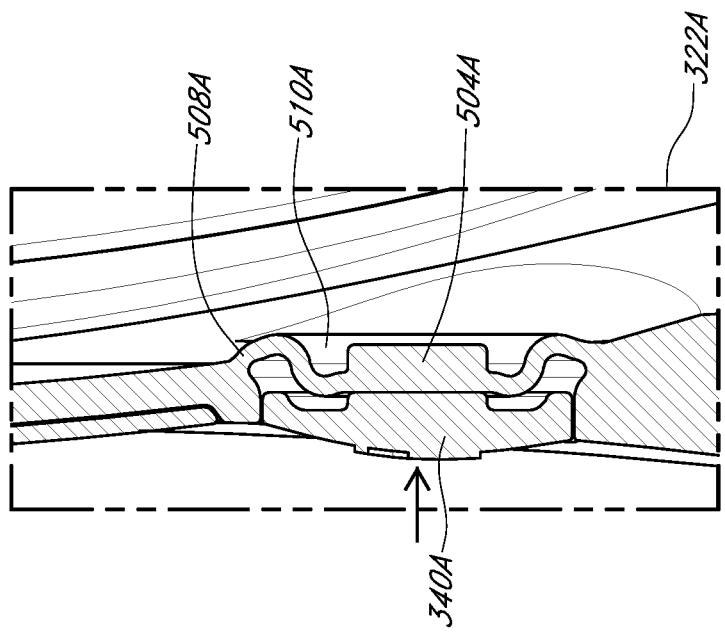

FIGS. 19A-19B show the flexible membrane 508A in an unactuated state. When unactuated (e.g., not pressed inward in a direction indicated by arrows in FIGS. 19A-19B), the flex portion 510A can extend away from the outer cover 322A and bend towards the toggle cover portion 340A. When the button 504A is actuated (e.g., pushed inward in a direction indicated by arrows in FIG. 19A-19B by a user pressing on the toggle cover portion 340A), the flex portion 510A of the flexible membrane 508A can flex inward (for example, in a direction indicated by arrows in FIGS. 19A-19B) and allow the button 504A to move inward relative to an inner surface of the cover 322A to engage and actuate the position lock control 150A as described above (e.g., shown in FIG. 4) to lock or unlock the prosthetic knee 110A. The flexible membrane 508A can differ for the button 504A on one side of the outer cover 322A relative to the button 504A on the opposite side of the outer cover 504A, as shown in FIGS. 19A-19B (e.g., one flexible membrane 508A can have a smaller length, causing it to flex less or have a shorter flex travel).

Figure 20:
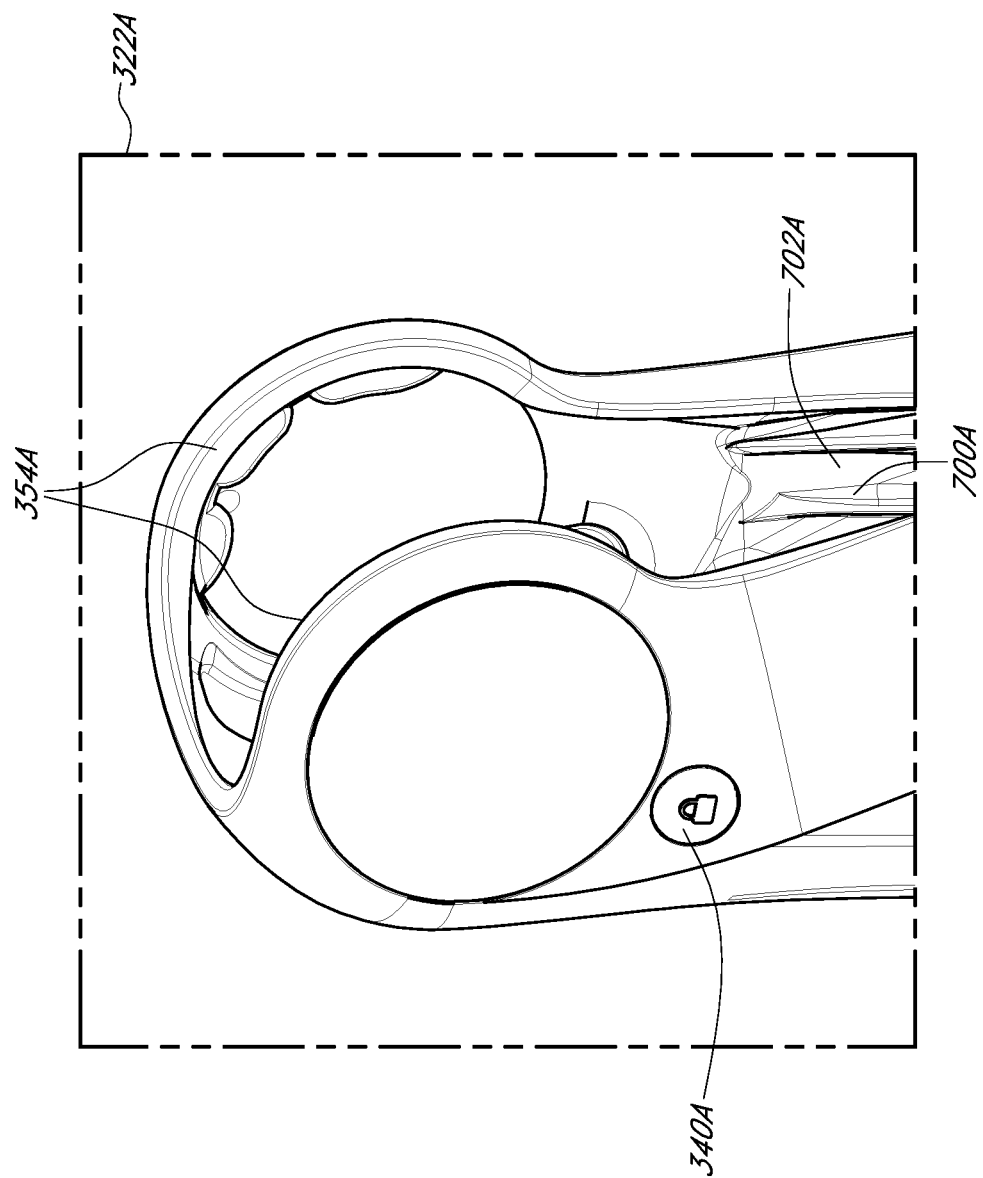
FIG. 20 is a perspective view of a portion of an outer cover.

FIG. 20 shows a schematic view of the outer cover 322A. Outer cover 322A differs from the outer cover 322 in that the edges 354A of sides of the outer cover 322A that couple to the side mounts 152A of the upper enclosure 120 are shorter (e.g., by a few millimeters) that the edges 354 of the outer cover 322.

Figure 21:
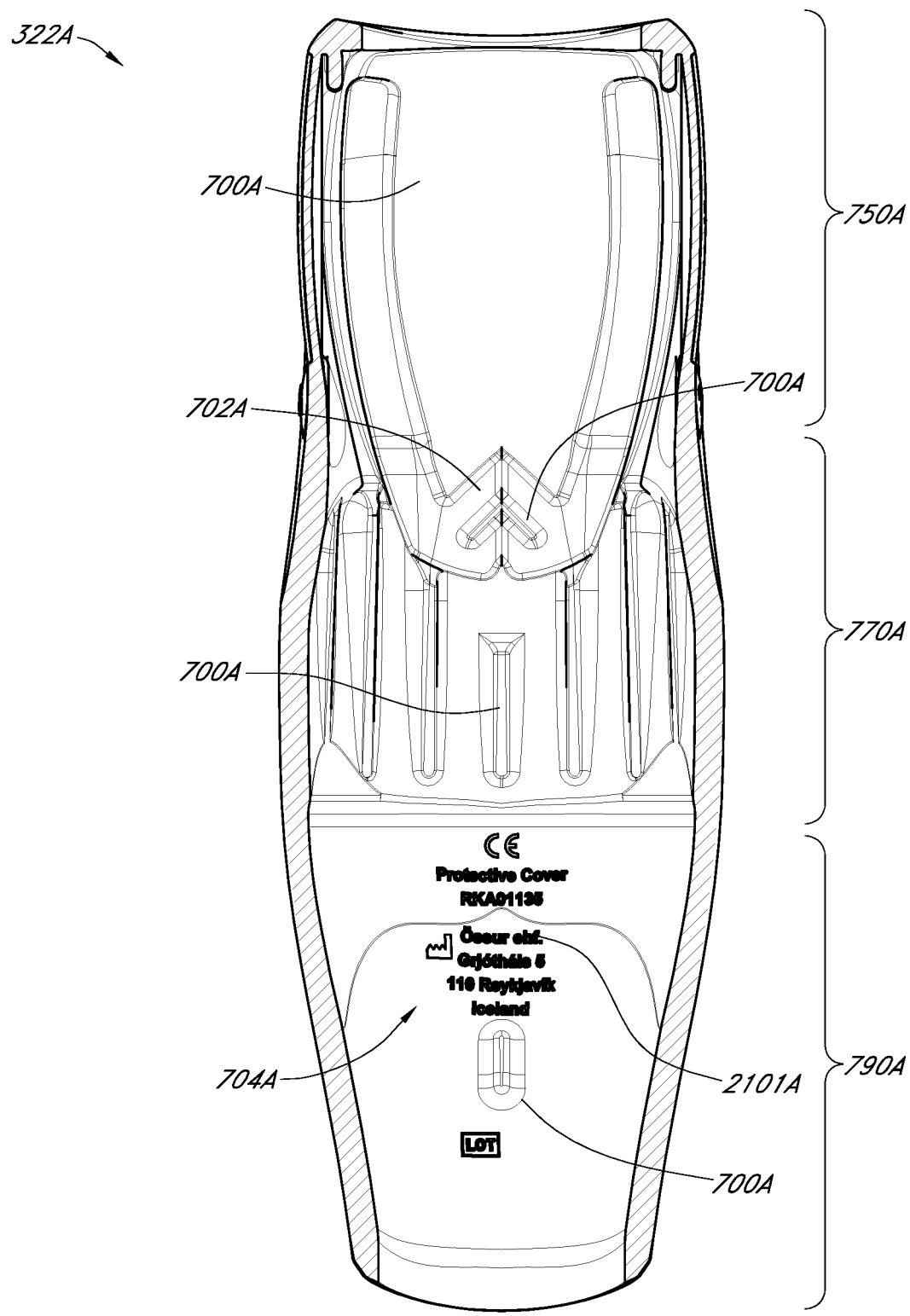
FIG. 21 is a cross-sectional rear view of an outer cover.

FIG. 21 illustrates a cross-sectional view of a front half of the outer cover 322A, according to one implementation. In the illustrated implementation, the outer cover 322A can include a number of raised portions 700A and a number of channels 702A (or cutouts) formed between raised portions 700A. The channels 702A can be formed vertically or at an angle to facilitate flow of water between the outer cover 322A and the prosthetic knee 110A (e.g., between the outer cover 322A and the upper or top housing 240 and the lower housing 246). A bottom portion 790A of the outer cover 322A can include a clearance portion 704A (e.g., recessed relative to surrounding inner surface of the outer cover 322A) that does not include any channels and can be spaced from the prosthetic knee 110A (e.g., form the upper or top housing 240 and the lower housing 246) during use (e.g., the clearance portion 704A can be positioned farther apart from a surface of the prosthetic knee 110A, such as upper or top housing 240 and the lower housing 246, than the top portion 750A and/or middle portion 770A of the cover 322A). The clearance 704A can further facilitate flow of water and prevent any water buildup between the outer cover 322A and the prosthetic knee 110A (e.g., between the outer cover 322A and the upper or top housing 240 and the lower housing 246). The front half of the outer cover 322A differs from the front half of the outer cover 322 as illustrated in FIG. 18A in that the top portion 750A of the outer cover 322A has fewer channels 702A (e.g., does not include four channels 702, has one channel 702A). The front half of the cover 322A optionally includes a label 2101A. As shown in FIG. 21, the outer cover 322A optionally has a raised portion 700A in the lower portion 790A. Though not shown, a raised portion (similar to raised portion 700A) can be on an opposite surface of the outer cover 322A (e.g., approximately diametrically aligned with the raised portion 700A shown in FIG. 21). Together, the raised portions 700A in the lower portion 790A of the outer cover 322A can facilitate the inner surface of the outer cover 322A (e.g., the clearance portion 704A) to be spaced from the prosthetic knee 110A (e.g., between the outer cover 322A and the upper or top housing 240 and the lower housing 246). In one implementation, one or both of the raised portions 700A in the lower portion 790A of the outer cover 322A can be excluded.

While certain embodiments of the inventions have been described, these embodiments have been presented by way of example only, and are not intended to limit the scope of the disclosure. Indeed, the novel methods and systems described herein may be embodied in a variety of other forms. Furthermore, various omissions, substitutions and changes in the systems and methods described herein may be made without departing from the spirit of the disclosure. The accompanying claims and their equivalents are intended to cover such forms or modifications as would fall within the scope and spirit of the disclosure. Accordingly, the scope of the present inventions is defined only by reference to the appended claims.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable sub-combination. Moreover, although features may be described above as acting in certain combinations, one or more features from a claimed combination can, in some cases, be excised from the combination, and the combination may be claimed as a sub-combination or variation of a sub-combination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

The scope of the present disclosure is not intended to be limited by the specific disclosures of preferred embodiments in this section or elsewhere in this specification and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

Of course, the foregoing description is that of certain features, aspects and advantages of the present invention, to which various changes and modifications can be made without departing from the spirit and scope of the present invention. Moreover, the devices described herein need not feature all of the objects, advantages, features and aspects discussed above. Thus, for example, those of skill in the art will recognize that the invention can be embodied or carried out in a manner that achieves or optimizes one advantage or a group of advantages as taught herein without necessarily achieving other objects or advantages as may be taught or suggested herein. In addition, while a number of variations of the invention have been shown and described in detail, other modifications and methods of use, which are within the scope of this invention, will be readily apparent to those of skill in the art based upon this disclosure. It is contemplated that various combinations or subcombinations of these specific features and aspects of embodiments may be made and still fall within the scope of the invention. Accordingly, it should be understood that various features and aspects of the disclosed embodiments can be combined with or substituted for one another in order to form varying modes of the discussed devices.

What is claimed is:

1. A prosthetic knee, comprising:
   an elongate frame configured to house electronics;
   an actuator movably coupled to a proximal portion of the elongate frame, the actuator being rotatable in an anterior-posterior direction about a medial-lateral axis, the actuator comprising an outer spline;
   a proximal connector coupled to the outer spline and configured to rotate with the outer spline about the medial-lateral axis;
   a distal connector coupled to a distal end of the elongate frame;
   one or more waterproof seals; and
   a waterproof cover assembly coupled to the actuator and the elongate frame, comprising
      an upper housing including an upper enclosure coupleable to a medial side and a lateral side of the actuator via the one or more waterproof seals, and
      a lower housing configured to enclose a distal portion of the elongate frame and configured to couple to the distal connector via the one or more waterproof seals.

2. The prosthetic knee of claim 1, wherein a proximal end of the lower housing is movably coupled to a distal end of the upper housing, and wherein one or more waterproof seals are disposed between the distal end of the upper housing and proximal end of the lower housing.

3. The prosthetic knee of claim 2, wherein the lower housing can translate between about 0.25-2.5 mm relative to the upper housing.

4. The prosthetic knee of claim 1, wherein a shaft of the actuator has a bore that communicates with a bore in the upper enclosure, the bore in the shaft of the actuator and the bore in the upper enclosure configured to receive one or more wires therethrough to electrically connect the electronics with the actuator.

5. The prosthetic knee of claim 1, wherein the proximal connector has drainage slots.

6. The prosthetic knee of claim 1, wherein the upper enclosure includes a medial side mount and lateral side mount, a first groove extending at least partially about a circumference of the medial side mount, a second groove extending at least partially about a circumference of the lateral side mount.

7. The prosthetic knee of claim 6, further comprising an outer cover removably coupleable to the upper enclosure and over the elongate frame, the outer cover comprising a proximal portion with a first lip configured to at least partially extend into the first groove and a second lip configured to at least partially extend into the second groove.

8. The prosthetic knee of claim 7, wherein a contour of the first lip corresponds to a contour of the first groove and a contour of the second lip corresponds to a contour of the second groove.

9. The prosthetic knee of claim 7, wherein the first and second grooves include an adaptor with one or more protrusions, and wherein a contour of the first and second lips includes one or more recesses so that the contour of the first and second lips corresponds to a contour of the adaptor.

10. The prosthetic knee of claim 9, wherein the adaptor is removably coupleable to the first and second grooves.

11. The prosthetic knee of claim 7, wherein an inner surface of the outer cover defines one or more channels or recesses for draining liquid that enters a space between the waterproof cover assembly and the outer cover.

12. The prosthetic knee of claim 7, wherein the outer cover further comprises a first side edge configured to releasably couple with a second side edge and wherein the first side edge and second side edge are flush with each other when coupled.

13. The prosthetic knee of claim 12, wherein the first side edge and second side edge releasably couple to each other via a plurality of magnets.

14. A prosthetic knee, comprising:
   an elongate frame configured to house electronics;
   an upper enclosure comprising an actuator coupled to a proximal portion of the elongate frame, the actuator being rotatable in an anterior-posterior direction about a medial-lateral axis, the upper enclosure including a medial side mount and lateral side mount, a first groove extending at least partially about a circumference of the medial side mount, a second groove extending at least partially about a circumference of the lateral side mount; and
   an outer cover coupled to the upper enclosure and over the elongate frame, the outer cover comprising a proximal portion comprising a first lip configured to at least partially extend into the first groove and a second lip configured to at least partially extend into the second groove to removably couple the proximal portion of the outer cover to the upper enclosure; and
   a closing interface comprising a first side and a second side configured to be separable from each other to receive the actuator and frame, and removably coupleable to each other to surround the frame.

15. The prosthetic knee of claim 14, wherein a contour of the first lip corresponds to a contour of the first groove and a contour of the second lip corresponds to a contour of the second groove.

16. The prosthetic knee of claim 14, wherein the first and second grooves include an adaptor with one or more protrusions, and wherein a contour of the first and second lips includes one or more recesses so that the contour of the first and second lips corresponds to a contour of the adaptor.

17. The prosthetic knee of claim 16, wherein the adaptor is removably coupleable to the first and second grooves.

18. The prosthetic knee of claim 14, wherein an inner surface of the outer cover defines one or more channels or recesses for draining liquid that enters a space between the elongate frame and the outer cover.

19. The prosthetic knee of claim 14, wherein the outer cover further comprises a first side edge configured to releasably couple with a second side edge and wherein the first side edge and second side edge are flush with each other when coupled.

20. The prosthetic knee of claim 19, wherein the first side edge and second side edge releasably couple to each other via a plurality of magnets.

\* \* \* \* \*